(12) United States Patent
Song et al.

(10) Patent No.: US 10,222,510 B2
(45) Date of Patent: Mar. 5, 2019

(54) ANTI-REFLECTIVE FILM

(71) Applicant: LG CHEM, LTD., Seoul (KR)

(72) Inventors: In Young Song, Daejeon (KR); Jin Seok Byun, Daejeon (KR); Boo Kyung Kim, Daejeon (KR); Seok Hoon Jang, Daejeon (KR); Yeong Rae Chang, Daejeon (KR); Sung Joon Oh, Daejeon (KR)

(73) Assignee: LG CHEM, LTD, Seoul (KR)

( * ) Notice: Subject to any disclaimer, the term of this patent is extended or adjusted under 35 U.S.C. 154(b) by 0 days.

(21) Appl. No.: 15/554,966

(22) PCT Filed: Mar. 9, 2017

(86) PCT No.: PCT/KR2017/002582
§ 371 (c)(1),
(2) Date: Aug. 31, 2017

(87) PCT Pub. No.: WO2017/155337
PCT Pub. Date: Sep. 14, 2017

(65) Prior Publication Data
US 2018/0106929 A1 Apr. 19, 2018

(30) Foreign Application Priority Data

Mar. 9, 2016 (KR) .................. 10-2016-0028468
Mar. 11, 2016 (KR) .................. 10-2016-0029336
(Continued)

(51) Int. Cl.
*G02B 1/115* (2015.01)
*C09D 5/00* (2006.01)
(Continued)

(52) U.S. Cl.
CPC .............. *G02B 1/11* (2013.01); *B05D 3/0254* (2013.01); *B05D 3/067* (2013.01); *B32B 7/02* (2013.01);
(Continued)

(58) Field of Classification Search
CPC ... G02B 1/00–1/18; C09D 5/006; C09D 7/67; C09D 135/02
See application file for complete search history.

(56) References Cited

U.S. PATENT DOCUMENTS 5,740,226 A  4/1998 Komiya et al.
6,633,392 B1 10/2003 Singh et al.
(Continued)

FOREIGN PATENT DOCUMENTS

CN  101285898 A  10/2008
CN  101765791 A  6/2010
(Continued)

OTHER PUBLICATIONS

Opalinska et al. "Size-dependent density of zirconia nanoparticles". Beilstein Journal of Nanotechnology, 6, (2015); pp. 27-35.*
(Continued)

*Primary Examiner* — Prashant J Khatri
(74) *Attorney, Agent, or Firm* — Rothwell, Figg, Ernst & Manbeck, P.C.

(57) ABSTRACT

Disclosed herein is an anti-reflective film including: a hard coating layer; and a low-refractive layer containing a binder resin, and hollow inorganic nanoparticles and solid inorganic nanoparticles which are dispersed in the binder resin, wherein the low-refractive layer includes a first layer containing at least 70 vol % of the entire solid inorganic nanoparticles and a second layer containing at least 70 vol % of the entire hollow inorganic nanoparticles, and at the time of fitting polarization ellipticity measured by ellipsom-
(Continued)

etry for the first layer or/and the second layer included in the low-refractive layer using a Cauchy model represented by the following General Equation 1, the second layer satisfies a predetermined condition.

21 Claims, 8 Drawing Sheets

(30)　　　　Foreign Application Priority Data

Mar. 14, 2016　(KR) .................. 10-2016-0030395
Mar. 9, 2017　(KR) .................. 10-2017-0029953

(51) Int. Cl.

| | | |
|---|---|---|
| C09D 7/40 | (2018.01) | |
| C09D 135/02 | (2006.01) | |
| B05D 3/02 | (2006.01) | |
| B05D 3/06 | (2006.01) | |
| G02B 1/14 | (2015.01) | |
| G02B 1/11 | (2015.01) | |
| B32B 7/02 | (2019.01) | |
| B32B 27/08 | (2006.01) | |
| B32B 27/18 | (2006.01) | |
| C08L 33/10 | (2006.01) | |
| G02B 1/113 | (2015.01) | |
| G02B 5/18 | (2006.01) | |
| C08C 19/40 | (2006.01) | |
| C09D 4/06 | (2006.01) | |
| C08L 83/04 | (2006.01) | |
| G01N 23/207 | (2018.01) | |
| C08J 7/04 | (2006.01) | |
| C09D 4/00 | (2006.01) | |
| C09D 5/33 | (2006.01) | |
| B05D 1/28 | (2006.01) | |
| C08K 3/36 | (2006.01) | |
| C08K 7/26 | (2006.01) | |
| C08K 7/18 | (2006.01) | |
| C09D 7/61 | (2018.01) | |
| C08K 3/01 | (2018.01) | |

(52) U.S. Cl.
CPC .............. *B32B 27/08* (2013.01); *B32B 27/18* (2013.01); *C08C 19/40* (2013.01); *C08J 7/042* (2013.01); *C08L 33/10* (2013.01); *C08L 83/04* (2013.01); *C09D 4/00* (2013.01); *C09D 4/06* (2013.01); *C09D 5/00* (2013.01); *C09D 5/004* (2013.01); *C09D 5/006* (2013.01); *C09D 7/67* (2018.01); *C09D 135/02* (2013.01); *G01N 23/207* (2013.01); *G02B 1/113* (2013.01); *G02B 1/115* (2013.01); *G02B 1/14* (2015.01); *G02B 5/18* (2013.01); *B05D 1/28* (2013.01); *C08J 2301/02* (2013.01); *C08J 2435/02* (2013.01); *C08K 3/01* (2018.01); *C08K 3/36* (2013.01); *C08K 7/18* (2013.01); *C08K 7/26* (2013.01); *C08K 2201/011* (2013.01); *C09D 7/61* (2018.01)

(56) References Cited

U.S. PATENT DOCUMENTS

| | | | |
|---|---|---|---|
| 7,335,698 B2 * | 2/2008 | Mano .................. | C08F 8/30 427/372.2 |
| 7,629,051 B2 | 12/2009 | Fukushige et al. | |
| 8,343,622 B2 | 1/2013 | Liu et al. | |
| 8,691,351 B2 | 4/2014 | Asakura et al. | |
| 8,795,825 B2 | 8/2014 | Kim et al. | |
| 9,310,525 B2 | 4/2016 | Shibuya et al. | |
| 2004/0044127 A1 | 3/2004 | Okubo et al. | |
| 2006/0007430 A1 | 1/2006 | Lotz et al. | |
| 2006/0274423 A1 | 12/2006 | Fukushige et al. | |
| 2007/0291367 A1 | 12/2007 | Hamamoto et al. | |
| 2008/0032053 A1 | 2/2008 | Kourtakis et al. | |
| 2010/0039708 A1 | 2/2010 | Suzuki et al. | |
| 2010/0196687 A1 | 8/2010 | Isono et al. | |
| 2012/0200933 A1 | 8/2012 | Akiyama et al. | |
| 2013/0088779 A1 | 4/2013 | Kang et al. | |
| 2013/0089178 A1 | 4/2013 | Mazor et al. | |
| 2013/0135726 A1 | 5/2013 | Wakizaka et al. | |
| 2013/0143028 A1 | 6/2013 | Asahi et al. | |
| 2013/0329297 A1 | 12/2013 | Hayashi et al. | |
| 2014/0016204 A1 | 1/2014 | Hakuta et al. | |
| 2014/0037741 A1 | 2/2014 | Armes et al. | |
| 2015/0079348 A1 | 3/2015 | Mizoshita et al. | |
| 2015/0152279 A1 * | 6/2015 | Kai .................. | C09D 201/00 428/216 |

FOREIGN PATENT DOCUMENTS

| | | |
|---|---|---|
| CN | 102119344 A | 7/2011 |
| CN | 102736138 A | 10/2012 |
| CN | 104458589 A | 3/2015 |
| EP | 3248776 A1 | 11/2017 |
| EP | 3385070 A1 | 10/2018 |
| JP | 2003142476 A | 5/2003 |
| JP | 2004212791 A | 7/2004 |
| JP | 2004255635 A | 9/2004 |
| JP | 2005-062350 A | 3/2005 |
| JP | 2005234003 A | 9/2005 |
| JP | 2007-011309 A | 1/2007 |
| JP | 2007078711 A | 3/2007 |
| JP | 2007098833 A | 4/2007 |
| JP | 2007272131 A | 10/2007 |
| JP | 2008107792 A | 5/2008 |
| JP | 2009163260 A | 7/2009 |
| JP | 2009217258 A | 9/2009 |
| JP | 2010084017 A | 4/2010 |
| JP | 2010085579 A | 4/2010 |
| JP | 2011-088787 A | 5/2011 |
| JP | 2011-102977 A | 5/2011 |
| JP | 2011248036 A | 12/2011 |
| JP | 2012-159744 A | 8/2012 |
| JP | 2012-198330 A | 10/2012 |
| JP | 2012-247606 A | 12/2012 |
| JP | 2013-008025 A | 1/2013 |
| JP | 2013205645 A | 10/2013 |
| JP | 5450708 B2 | 3/2014 |
| JP | 2014-074779 A | 4/2014 |
| JP | 2014-240929 A | 12/2014 |
| JP | 2015072464 A | 4/2015 |
| JP | 2015-108733 A | 6/2015 |
| JP | 2015-232614 A | 12/2015 |
| JP | 2017-021293 A | 1/2017 |
| JP | 2017-040936 A | 2/2017 |
| JP | 2017-049313 A | 3/2017 |
| JP | 2018-123043 A | 8/2018 |
| KR | 20060046318 A | 5/2006 |
| KR | 20080050335 A | 6/2008 |
| KR | 20090046873 A | 5/2009 |
| KR | 20090105545 A | 10/2009 |
| KR | 20100039869 A | 4/2010 |
| KR | 100960442 B1 | 5/2010 |
| KR | 20110060810 A | 6/2011 |
| KR | 20110121233 A | 11/2011 |
| KR | 20120093212 A | 8/2012 |
| KR | 101194180 B1 | 10/2012 |
| KR | 10-1226228 B1 | 1/2013 |
| KR | 20130120223 A | 11/2013 |
| KR | 20140006876 A | 1/2014 |
| KR | 20140006922 A | 1/2014 |
| KR | 101378603 B1 | 3/2014 |
| KR | 20140037080 A | 3/2014 |
| KR | 20140050538 A | 4/2014 |
| KR | 10-2015-0120264 A | 10/2015 |
| TW | 200807014 A | 2/2008 |
| TW | 200833763 A | 8/2008 |

(56) References Cited

FOREIGN PATENT DOCUMENTS

| TW | 201011356 A | 3/2010 |
|---|---|---|
| TW | 201128215 A | 8/2011 |
| TW | 201221599 A | 6/2012 |
| TW | 201606357 A | 2/2016 |
| WO | 2009120983 A2 | 10/2009 |
| WO | 2017-122953 A1 | 7/2017 |
| WO | 2017-157682 A1 | 9/2017 |

OTHER PUBLICATIONS

Kimoto et al. "Effective Density of Silica Nanoparticle Size Standards". 2014 International Aerosol Conference, (2014); p. 1.*
Extended European Search Report issued in European patent application No. 17763598.4 dated Aug. 1, 2018, 8 pages.
Extended European Search Report issued in European patent application No. 17733956.1 dated Sep. 3, 2018, 6 pages.
Extended European Search Report issued for European Patent Application No. 17763596.8 dated Nov. 29, 2018, 9 pages.

* cited by examiner

[Fig 1]
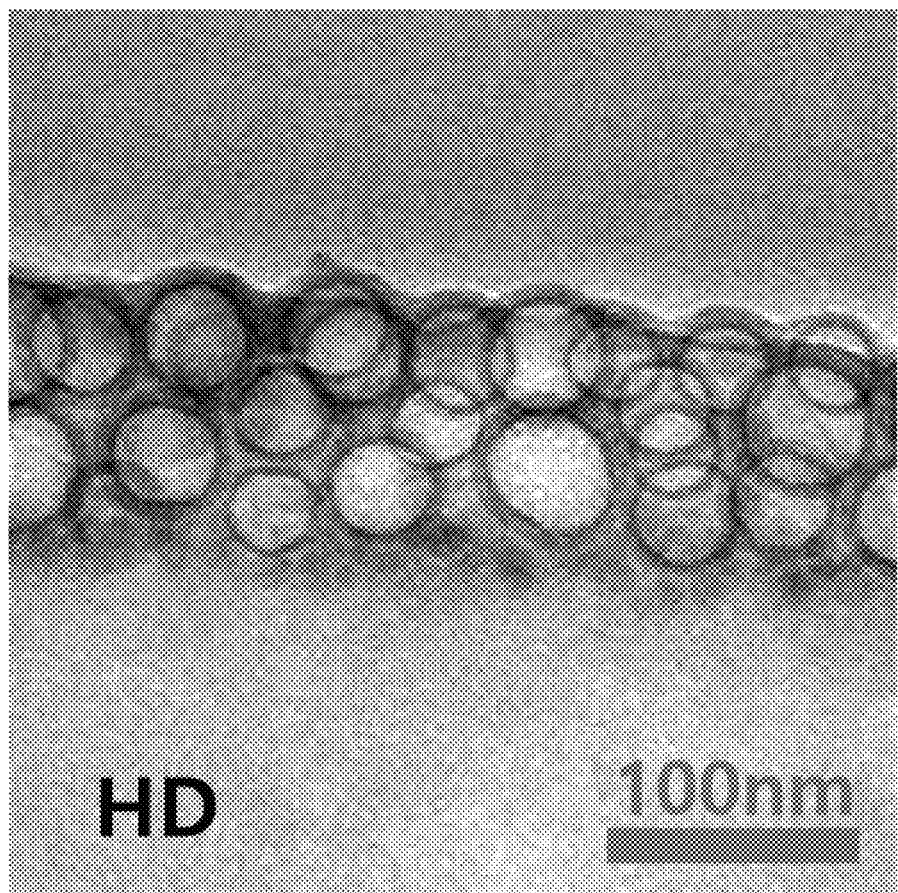

[Fig 2]
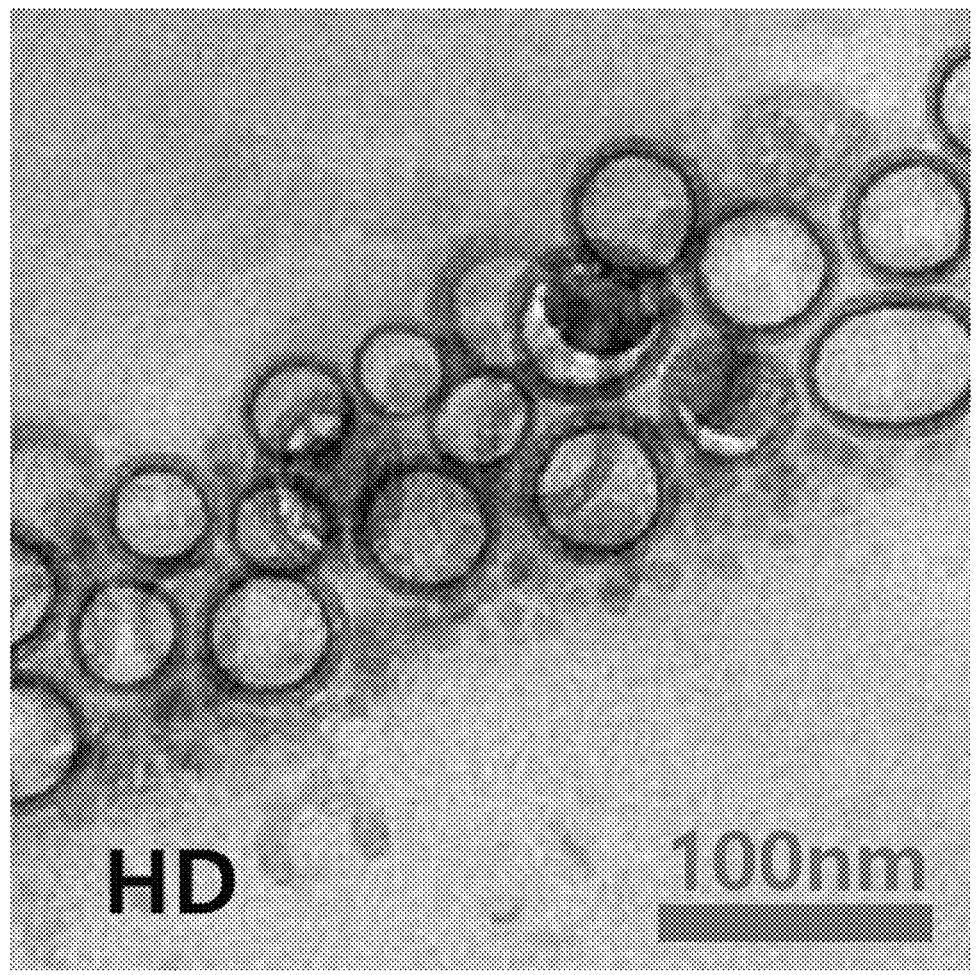

[Fig 3]
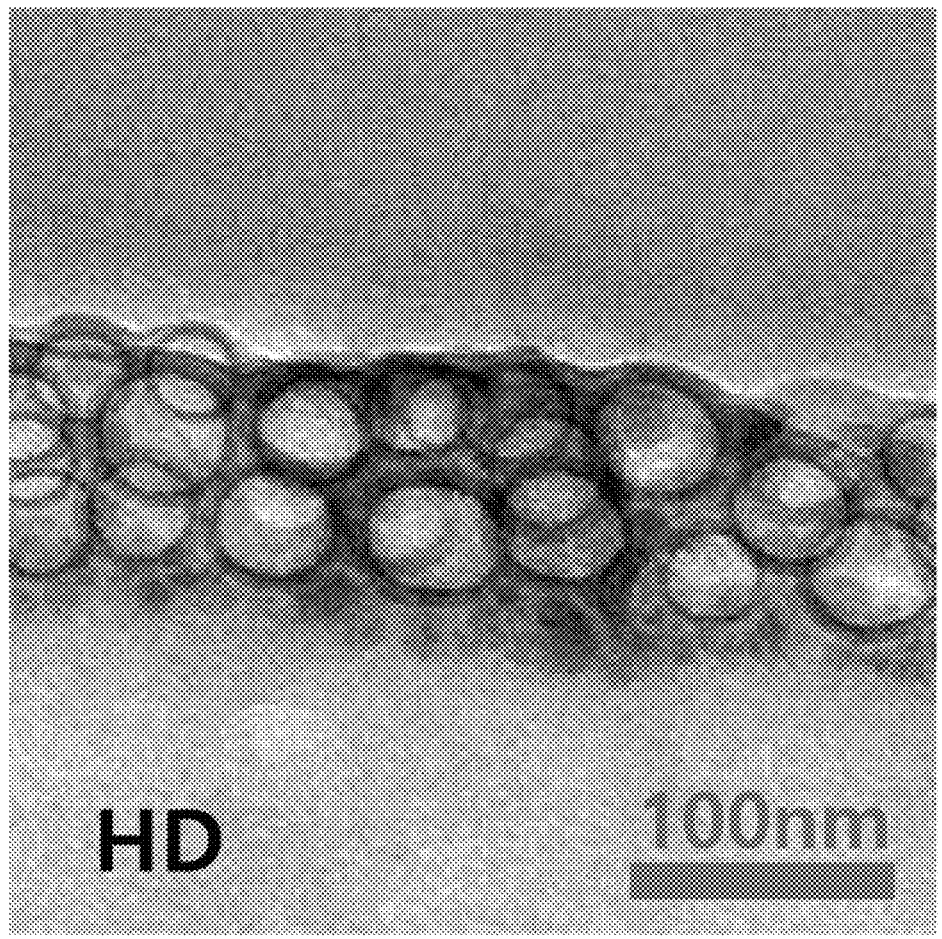

[Fig 4]
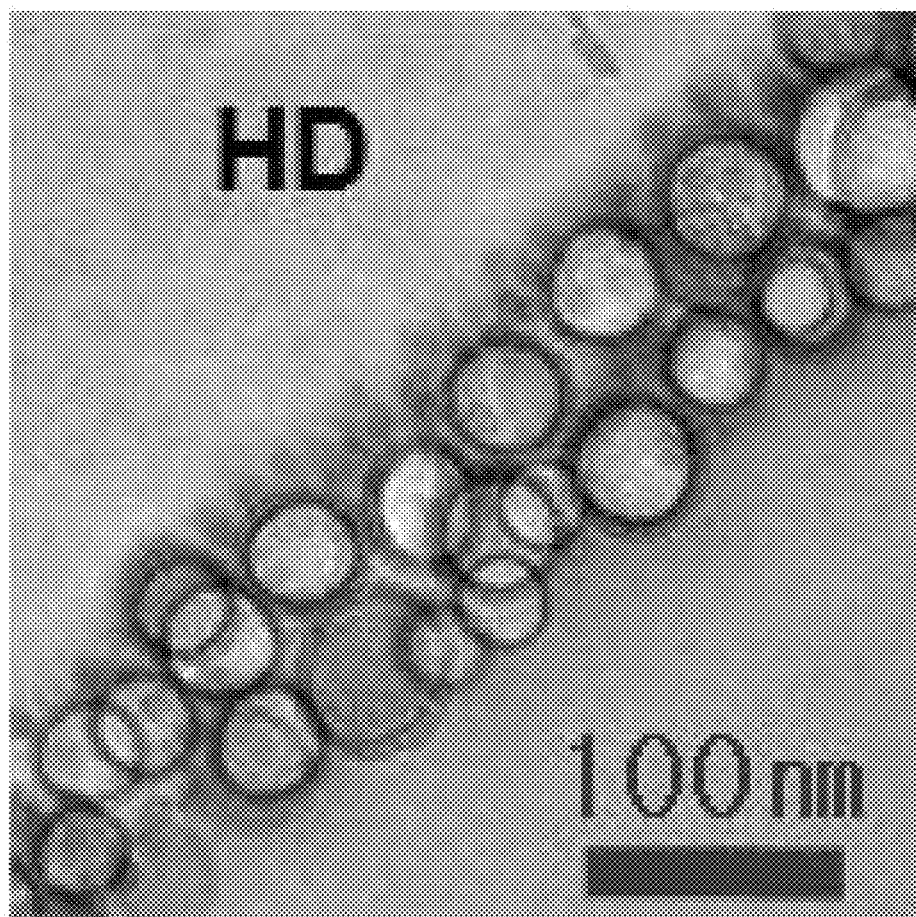

[Fig 5]
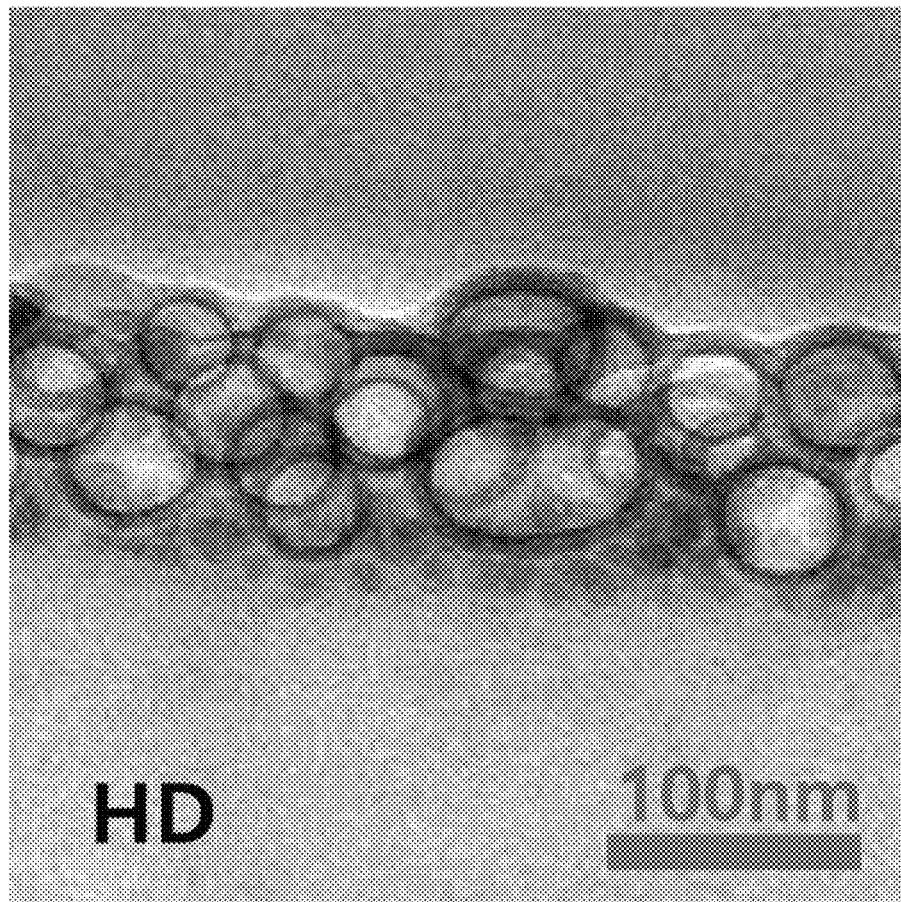

[Fig 6]
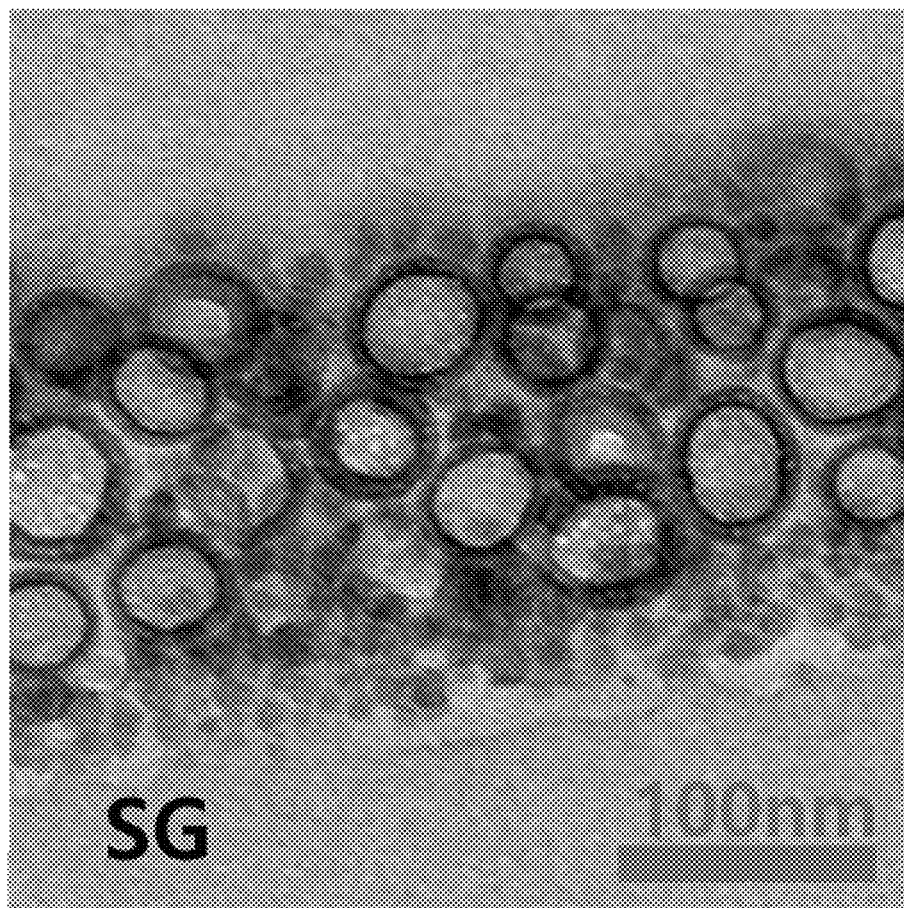

[Fig 7]
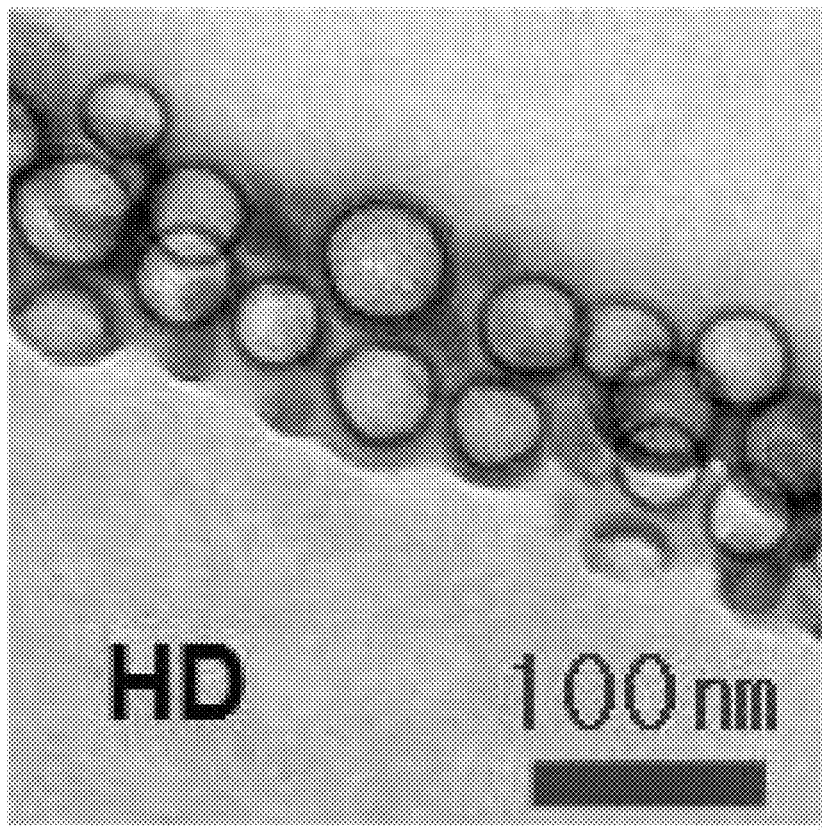

[Fig 8]
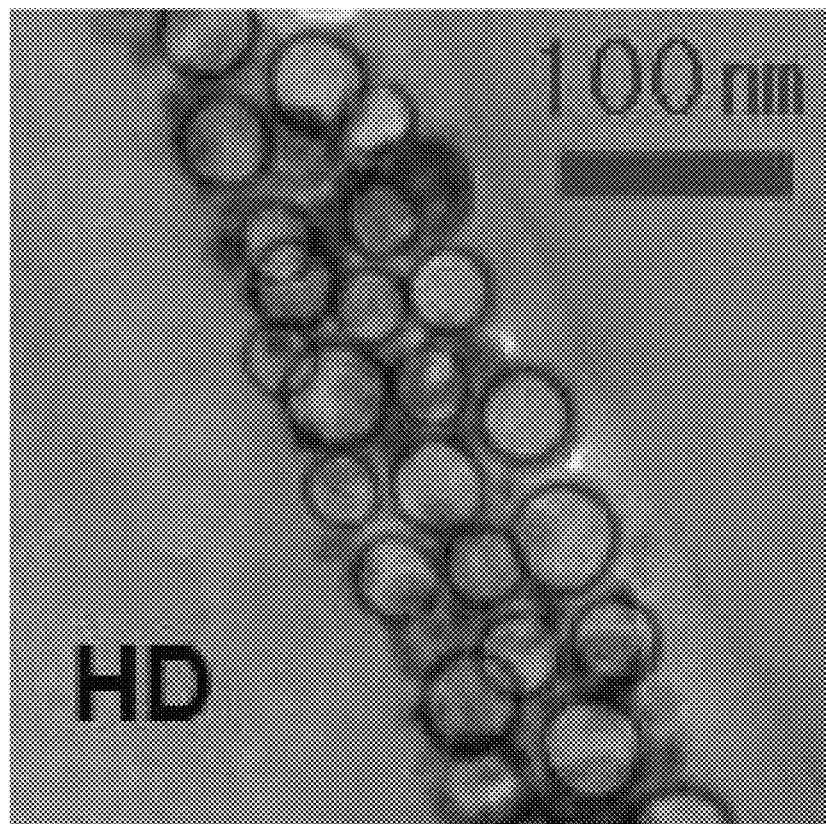

ANTI-REFLECTIVE FILM

CROSS-REFERENCE TO RELATED APPLICATION

This application is a National Stage Entry of International Application No. PCT/KR2017/002582, filed on Mar. 9, 2017, and claims the benefit of and priority to Korean Application No. 10-2016-0028468, filed on Mar. 9, 2016, Korean Application No. 10-2016-0029336, filed on Mar. 11, 2016, Korean Application No. 10-2016-0030395, filed on Mar. 14, 2016, and Korean Application No. 10-2017-0029953, filed on Mar. 9, 2017 all of which are hereby incorporated by reference in their entirety for all purposes as if fully set forth herein.

FIELD OF THE INVENTION

The present invention relates to an anti-reflective film. More particularly, the present invention relates to an anti-reflective film capable of having low reflectance and high light transmittance, simultaneously implementing scratch-resistance and an anti-pollution property, and enhancing sharpness of a screen of a display device.

BACKGROUND OF THE INVENTION

In general, an anti-reflective film is mounted on a flat-panel display device such as a plasma display panel (PDP), a liquid crystal display (LCD), and the like, in order to minimize reflection of light incident from the outside.

As a method for minimizing reflection of light, there are a method of dispersing fillers such as inorganic fine particles in a resin and coating the resin on a substrate film to impart unevenness (i.e. an anti-glare (AG) coating method), a method of forming a plurality of layers having different refractive indices on a substrate film to use light interference (i.e. an anti-reflection (AR) coating method), a combination of these methods, and the like.

Among them, in the case of the AG coating method, an absolute amount of reflected light is equivalent to that in a general hard coating method, but it is possible to obtain a low-reflection effect by decreasing an amount of light entering the eyes using scattering of the light through unevenness. However, since in the AG coating method, sharpness of a screen is deteriorated due to surface unevenness, recently, the AR coating method has been variously studied.

As a film using the AR coating method, a film having a multilayer structure in which a hard coating layer (a high-refractive index layer), a low-reflective coating layer, and the like are laminated on a substrate film has been commercialized. However, in the method of forming a plurality of layers as described above, since a process of forming each of the layers is separately performed, close interlayer adhesion (interfacial adhesion) may be weak, such that scratch resistance may be deteriorated.

Further, in order to improve scratch resistance of the low-refractive layer included in the anti-reflective film, a method of adding various particles with a nanometer size (for example, silica particles, alumina particles, zeolite particles, or the like) was mainly conducted in the past. However, in the case of using the particles with a nanometer size, it was difficult to increase scratch resistance while decreasing reflectance of the low-refractive layer, and an anti-pollution property of a surface of the low-refractive layer was significantly deteriorated due to the particles with the nanometer size.

Therefore, various studies for decreasing an absolute reflection amount of light incident from the outside and improving an anti-pollution property together with scratch resistance of a surface have been conducted, but physical properties of the anti-reflective film are not sufficiently improved in spite of these studies.

DETAILED DESCRIPTION OF THE INVENTION

Technical Problem

It is an object of the present invention to provide an anti-reflective film having advantages of having low reflectance and high light transmittance, while simultaneously implementing scratch-resistance and an anti-pollution property, and enhancing sharpness of a screen of a display device.

Technical Solution

There is provided an anti-reflective film including: a hard coating layer; and a low-refractive layer containing a binder resin, and hollow inorganic nanoparticles and solid inorganic nanoparticles which are dispersed in the binder resin, wherein the low-refractive layer includes a first layer containing at least 70 vol % of the entire solid inorganic nanoparticles and a second layer containing at least 70 vol % of the entire hollow inorganic nanoparticles, and at the time of fitting polarization ellipticity measured by ellipsometry for the second layer included in the low-refractive layer using a Cauchy model represented by the following General Equation 1, the second layer satisfies the following conditions: A is 1.0 to 1.50, B is 0 to 0.007, and C is 0 to $1*10^{-3}$.

$$n(\lambda) = A + \frac{B}{\lambda^2} + \frac{C}{\lambda^4} \qquad \text{[General Equation 1]}$$

In General Equation 1, $n(\lambda)$ is a refractive index at a wavelength of $\lambda$, $\lambda$ is in a range of 300 nm to 1800 nm, and A, B, and C are Cauchy parameters.

There is also provided an anti-reflective film including: a hard coating layer; and a low-refractive layer containing a binder resin, and hollow inorganic nanoparticles and solid inorganic nanoparticles which are dispersed in the binder resin, wherein the low-refractive layer includes a first layer containing at least 70 vol % of the entire solid inorganic nanoparticles and a second layer containing at least 70 vol % of the entire hollow inorganic nanoparticles, and at the time of fitting polarization ellipticity measured by ellipsometry for the first layer included in the low-refractive layer using a Cauchy model represented by the following General Equation 1, the first layer satisfies the following conditions: A is 1.0 to 1.65.

$$n(\lambda) = A + \frac{B}{\lambda^2} + \frac{C}{\lambda^4} \qquad \text{[General Equation 1]}$$

In General Equation 1, $n(\lambda)$ is a refractive index at a wavelength of $\lambda$, $\lambda$ is in a range of 300 nm to 1800 nm, and A, B, and C are Cauchy parameters.

In addition, There is also provided an anti-reflective film including: a hard coating layer; and a low-refractive layer containing a binder resin, and hollow inorganic nanoparticles and solid inorganic nanoparticles which are dispersed in the binder resin, wherein the low-refractive layer includes a first layer containing at least 70 vol % of the entire solid inorganic nanoparticles and a second layer containing at least 70 vol % of the entire hollow inorganic nanoparticles, and at the time of fitting polarization ellipticity measured by ellipsometry for the first layer and the second layer included in the low-refractive layer using a Cauchy model represented by the following General Equation 1, the difference between the A value for the first layer and the A value for the second layer is 0.100 to 0.200.

$$n(\lambda) = A + \frac{B}{\lambda^2} + \frac{C}{\lambda^4}$$ [General Equation 1]

In General Equation 1, $n(\lambda)$ is a refractive index at a wavelength of $\lambda$, $\lambda$ is in a range of 300 nm to 1800 nm, and A, B, and C are Cauchy parameters.

Hereinafter, the anti-reflective film according to exemplary embodiments of the present invention will be described in more detail.

As used herein, the term "photopolymerizable compound" collectively refers to compounds causing a polymerization reaction when light, for example, visible light or UV light, is irradiated thereto.

Further, the term "fluorine-containing compound" refers to a compound in which at least one fluorine element is contained.

In addition, the term "(meth)acryl" is used as a concept including both acryl and methacryl.

In addition, the term "(co)polymer" is used as a concept including both a co-polymer and a homo-polymer.

Further, the term "hollow silica particles" means silica particles derived from a silicon compound or an organic silicon compound in a shape in which an empty space is present on surfaces and/or insides of silica particles.

According to the exemplary embodiment of the present invention, there is provided an anti-reflective film including: a hard coating layer; and a low-refractive layer containing a binder resin, and hollow inorganic nanoparticles and solid inorganic nanoparticles which are dispersed in the binder resin, wherein the low-refractive layer includes a first layer containing at least 70 vol % of the entire solid inorganic nanoparticles and a second layer containing at least 70 vol % of the entire hollow inorganic nanoparticles, and at the time of fitting polarization ellipticity measured by ellipsometry for the second layer included in the low-refractive layer using the Cauchy model represented by the following General Equation 1, the second layer satisfies the following conditions: A is 1.0 to 1.50, B is 0 to 0.007, and C is 0 to $1*10^{-3}$.

In the past, in order to increase scratch resistance of an anti-reflective film, an excess amount of inorganic particles was added, but there was a limitation in increasing the scratch resistance of the anti-reflective film, and reflectance and an anti-pollution property were rather deteriorated.

Therefore, the present inventors conducted research into an anti-reflective film and confirmed through experiments that in the case of distributing hollow inorganic nanoparticles and solid inorganic nanoparticles so as to be distinguished from each other in a low-refractive layer included in the anti-reflective film, the anti-reflective film may have low reflectance and high light transmittance and simultaneously implement high scratch resistance and anti-pollution properties, thereby completing the present invention.

More specifically, the anti-reflective film may include: the hard coating layer; and the low-refractive layer containing the binder resin, and the hollow inorganic nanoparticles and solid inorganic nanoparticles which are dispersed in the binder resin, wherein the low-refractive layer includes the first layer containing at least 70 vol % of the entire solid inorganic nanoparticles and the second layer containing at least 70 vol % of the entire hollow inorganic nanoparticles.

At the time of measuring the polarization ellipticity using ellipsometry and fitting the measured data by the Cauchy model, the low-refractive layer including the first layer containing at least 70 vol % of the entire solid inorganic nanoparticles and the second layer containing at least 70 vol % of the entire hollow inorganic nanoparticles may exhibit unique Cauchy parameter values.

In detail, at the time of fitting the polarization ellipticity measured by ellipsometry for the second layer included in the low-refractive layer using the Cauchy model represented by the following General Equation 1, the second layer may satisfy the following conditions: A is 1.0 to 1.50, B is 0 to 0.007, and C is 0 to $1*10^{-3}$.

In addition, at the time of fitting the polarization ellipticity measured by ellipsometry for the second layer included in the low-refractive layer using the Cauchy model represented by the following General Equation 1, the second layer may satisfy the following conditions: A is 1.10 to 1.40, 1.20 to 1.35, or 1.211 to 1.349, B is 0 to 0.007, 0 to 0.00550, or 0 to 0.00513, and C is 0 to $1*10^{-3}$, 0 to $5.0*10^{-4}$, or 0 to $4.8685*10^{-4}$.

$$n(\lambda) = A + \frac{B}{\lambda^2} + \frac{C}{\lambda^4}$$ [General Equation 1]

In General Equation 1, $n(\lambda)$ is a refractive index at a wavelength of $\lambda$, $\lambda$ is in a range of 300 nm to 1800 nm, and A, B, and C are Cauchy parameters.

In detail, at the time of fitting the polarization ellipticity measured by ellipsometry for the first layer included in the low-refractive layer using the Cauchy model represented by General Equation 1, the first layer satisfies the following conditions: A is 1.0 to 1.65, B is 0.0010 to 0.0350, and C is 0 to $1*10^{-3}$.

In addition, at the time of fitting the polarization ellipticity measured by ellipsometry for the first layer included in the low-refractive layer using the Cauchy model represented by General Equation 1, the first layer satisfies the following conditions: A is 1.30 to 1.55, 1.40 to 1.52, or 1.491 to 1.511, B is 0 to 0.005, 0 to 0.00580, or 0 to 0.00573, and C is 0 to $1*10^{-3}$, 0 to $5.0*10^{-4}$, or 0 to $4.1352*10^{-4}$.

The polarization ellipticity measured by ellipsometry and related data (ellipsometry data ($\psi$, $\Delta$)) may be measured by a method and an apparatus generally known in the art. For example, linear polarization of the first and second layers included in the low-refractive layer may be measured in a wavelength range of 380 nm to 1000 nm at an incident angle of 70° using an ellipsometer (J. A. Woollam Co. M-2000). The measured linear polarization data (ellipsometry data ($\psi$, $\Delta$)) may be separately applied to the first and second layers using Complete EASE software to thereby be fitted by the Cauchy model represented by General Equation 1 so that a mean-squared error (MSE) is 3 or less.

The Cauchy parameters A, B, and C in each of the first and second layers included in the low-refractive layer described above are associated with changes in the refractive index and the extinction coefficient depending on the wavelength, respectively. In the case in which the second layer included in the low-refractive layer satisfies ranges of the Cauchy parameters A, B, and C determined in fitting results using the Cauchy model represented by General Equation 1 described above, the second layer may maintain a fitted electron density and reflectance distribution therein, such that the anti-reflective film may implement lower reflectance and have a relatively stable structure against scratches or external contamination materials. In detail, the Cauchy parameter A is associated with a minimum refractive index at each wavelength, and B and C are associated with a decrease degree of the refractive index depending on an increase in the wavelength.

Further, in the case in which each of the first and second layers included in the low-refractive layer satisfies ranges of the Cauchy parameters A, B, and C determined in fitting results using the Cauchy model represented by General Equation 1 described above, the above-mentioned effect may be further improved and maximized.

According to the other example embodiment of the present invention, there is provided an anti-reflective film including: a hard coating layer; and a low-refractive layer containing a binder resin, and hollow inorganic nanoparticles and solid inorganic nanoparticles which are dispersed in the binder resin, wherein the low-refractive layer includes a first layer containing at least 70 vol % of the entire solid inorganic nanoparticles and a second layer containing at least 70 vol % of the entire hollow inorganic nanoparticles, and at the time of fitting polarization ellipticity measured by ellipsometry for the first layer included in the low-refractive layer using a Cauchy model represented by the following General Equation 1, the first layer satisfies the following conditions: A is 1.0 to 1.65.

$$n(\lambda) = A + \frac{B}{\lambda^2} + \frac{C}{\lambda^4}$$ [General Equation 1]

In General Equation 1, n(λ) is a refractive index at a wavelength of λ, λ is in a range of 300 nm to 1800 nm, and A, B, and C are Cauchy parameters.

The Cauchy parameter A is associated with a minimum refractive index at each wavelength. As the Cauchy parameter A for the first layer included in the low-refractive layer satisfies 1.0 to 1.65, 1.30 to 1.55, 1.40 to 1.52, 1.480 to 1.515, or 1.491 to 1.511, the anti-reflective film of the another example embodiment can maintain an optimized refractive index distribution therein, thereby realizing lower reflectance in a required wavelength range.

The polarization ellipticity measured by ellipsometry and related data (Ellipsometry data (ψ, Δ)) may be measured by the method stated in the anti-reflective film of the example embodiment of the present invention above.

Specifically, the polarization ellipticity measured by ellipsometry can be determined by measuring linear polarization in a wavelength range of 380 nm to 1000 nm at an incident angle of 70°.

According to another example embodiment of the present invention, there is provided an anti-reflective film including: a hard coating layer; and a low-refractive layer containing a binder resin, and hollow inorganic nanoparticles and solid inorganic nanoparticles which are dispersed in the binder resin, wherein the low-refractive layer includes a first layer containing at least 70 vol % of the entire solid inorganic nanoparticles and a second layer containing at least 70 vol % of the entire hollow inorganic nanoparticles, and at the time of fitting polarization ellipticity measured by ellipsometry for the first layer and the second layer included in the low-refractive layer using a Cauchy model represented by the following General Equation 1, the difference between the A value for the first layer and the A value for the second layer is 0.100 to 0.200.

$$n(\lambda) = A + \frac{B}{\lambda^2} + \frac{C}{\lambda^4}$$ [General Equation 1]

In General Equation 1, n(λ) is a refractive index at a wavelength of λ, λ is in a range of 300 nm to 1800 nm, and A, B, and C are Cauchy parameters.

The Cauchy parameter A is associated with a minimum refractive index at each wavelength. As the difference between the A value for the first layer and the A value for the second layer is 0.100 to 0.200, 0.120 to 0.190, 0.140 to 0.180, or 0.145 to 0.177, the antireflection film of this embodiment can greatly improve the mechanical properties of the outer surface while maintaining an optimized refractive index distribution, thereby realizing lower reflectance and having a relatively stable structure against scratches or external contaminants.

Specifically, at the time of fitting the polarization ellipticity measured by ellipsometry for the first layer included in the low-refractive layer using the Cauchy model represented by General Equation 1, the first layer satisfies the following conditions: A may be 1.0 to 1.65, 1.30 to 1.55, 1.40 to 1.52, or 1.491 to 1.511.

In addition, at the time of fitting the polarization ellipticity measured by ellipsometry for the second layer included in the low-refractive layer using the Cauchy model represented by the following General Equation 1, the second layer may satisfy the following conditions: A may be 1.0 to 1.50, 1.10 to 1.40, 1.20 to 1.35, or 1.211 to 1.349.

The polarization ellipticity measured by ellipsometry and related data (ellipsometry data (ψ, Δ)) may be measured by the method stated in the anti-reflective film of the example embodiment of the present invention above.

Specifically, the polarization ellipticity measured by ellipsometry can be determined by measuring linear polarization in a wavelength range of 380 nm to 1000 nm at an incident angle of 70°.

Hereinafter, the specific contents of the antireflection film of the above embodiment(s) will be described.

Meanwhile, in the anti-reflective film according to the exemplary embodiment, the low-refractive layer may include a first layer containing at least 70 vol % of the entire solid inorganic nanoparticles and a second layer containing at least 70 vol % of the entire hollow inorganic nanoparticles, wherein the first layer may be positioned to be closer to the interface between the hard coating layer and the low-refractive layer than the second layer.

In the low-refractive layer of the anti-reflective film, the solid inorganic nanoparticles are mainly distributed in a region close to the interface between the hard coating layer and the low-refractive layer, and the hollow inorganic nanoparticles are mainly distributed in a region opposite to the interface, wherein the regions in which the solid inorganic nanoparticles and the hollow inorganic nanoparticles are mainly distributed, respectively, may form individual layers which may be visibly confirmed in the low-refractive layer.

More specifically, in the case of mainly distributing the solid inorganic nanoparticles in the region of the low-refractive layer of the anti-reflective film close to the interface between the hard coating layer and the low-refractive layer and mainly distributing the hollow inorganic nanoparticles in the region of the low-refractive layer opposite to the interface, it is possible to achieve lower reflectance than an actual reflectance which could be obtained using the inorganic particles in the past, and the low-refractive layer may simultaneously implement significantly improved scratch resistance and anti-pollution properties.

In addition, the first layer containing at least 70 vol % of the entire solid inorganic nanoparticles may be located within 50% of the total thickness of the low-refractive layer from the interface between the hard coating layer and the low-refractive layer.

More specifically, the first layer containing at least 70 vol % of the entire solid inorganic nanoparticles may be located within 30% of the total thickness of the low refractive layer from the interface between the hard coating layer and the low-refractive layer.

Further, as described above, the hollow inorganic nanoparticles may be mainly distributed in the region of the low-refractive layer opposite to the interface between the hard coating layer and low-refractive layer. In detail, at least 30 vol % of the entire hollow inorganic nanoparticles may be present at a distance farther than that of the entire solid inorganic nanoparticles from the interface between the hard coating layer and low-refractive layer in a thickness direction of the low-refractive layer. Accordingly, as described above, the first layer may be positioned closer to the interface between the hard coating layer and the low-refractive layer than the second layer.

As described above, it can be visually confirmed that each of the first layer and the second layer, in which the solid inorganic nanoparticles and the hollow inorganic nanoparticles are mainly distributed, respectively, is present in the low-refractive layer.

For example, it can be visually confirmed that each of the first layer and the second layer is present in the low refractive layer by using a transmission electron microscope or a scanning electron microscope. Further, the ratio of the solid inorganic nanoparticles and the hollow inorganic nanoparticles distributed in the first layer and the second layer in the low-refractive layer can also be confirmed.

Meanwhile, each of the first layer containing at least 70 vol % of the entire solid inorganic nanoparticles and the second layer containing at least 70 vol % of the entire hollow inorganic nanoparticles share a common optical property in one layer, and thus can be defined as a single layer.

Specifically, at the time of fitting polarization ellipticity measured by ellipsometry for the first layer and the second layer included in the low-refractive layer using a Cauchy model represented by the above General Equation 1, they have specific Cauchy parameters A, B, and C so that the first and second layers can be distinguished from each other.

Also, since the thicknesses of the first layer and the second layer can be derived through fitting the ellipticity of the polarization measured by the ellipsometry with a Cauchy model represented by the above General Equation 1, the first layer and the second layer in the low refractive layer can be defined.

Meanwhile, at the time of fitting polarization ellipticity measured by ellipsometry using a Cauchy model represented by the above General Equation 1, the Cauchy parameters A, B, and C may be an average value in one layer.

Accordingly, when there is an interface between the first layer and the second layer, there may be a region where the first layer and the second layer overlap with the Cauchy parameters A, B, and C.

However, even in this case, the thickness and the position of the first layer and the second layer can be specified along the region satisfying the average value of the Cauchy parameters A, B, and C of each of the first layer and the second layer.

"At least 70 vol % of the entire solid inorganic nanoparticles are present in a specific region" means that most of the solid inorganic nanoparticles are present in the specific region in a cross-section of the low-refractive layer. In detail, at least 70 vol % of the entire solid inorganic nanoparticles may be confirmed by measuring a total volume of the solid inorganic nanoparticles.

Whether or not the hollow inorganic nanoparticles and the solid inorganic nanoparticles are present in specific regions may be determined by whether each of the hollow inorganic nanoparticles or each of the solid inorganic nanoparticles is present in the specific region, except for particles present on an interface of the specific region.

As the solid inorganic nanoparticles are mainly distributed in the region of the low-refractive layer of the anti-reflective film close to the interface between the hard coating layer and the low-refractive layer and the hollow inorganic nanoparticles are mainly distributed in the region of the low-refractive layer opposite to the interface, two or more portions or two or more layers having different refractive indices may be formed in the low-refractive layer, and thus the reflectance of the anti-reflective film may be decreased.

Specific distribution of the solid inorganic nanoparticles and the hollow inorganic nanoparticles in the low-refractive layer may be obtained by adjusting a density difference between the solid inorganic nanoparticles and the hollow inorganic nanoparticles and adjusting a drying temperature of a photocurable resin composition for forming a low-refractive layer, containing the two kinds of nanoparticles as described above, in a specific manufacturing method to be described below.

In detail, a density of the solid inorganic nanoparticles may be at least 0.50 g/cm$^3$ higher than that of the hollow inorganic nanoparticles, the difference in density between the solid inorganic nanoparticles and the hollow inorganic nanoparticles may be 0.50 g/cm$^3$ to 1.50 g/cm$^3$, or 0.60 g/cm$^3$ to 1.00 g/cm$^3$. Due to this density difference, the solid inorganic nanoparticles may be positioned in the low-refractive layer formed on the hard coating layer to be closer to the hard coating layer.

However, as can be seen from the production method and examples described later, it is necessary to implement a predetermined drying temperature and time to achieve the distribution of particles in the low refraction layer in spite of the difference in density between the two kinds of particles In the case of mainly distributing the solid inorganic nanoparticles in the region of the low-refractive layer of the anti-reflective film close to the interface between the hard coating layer and the low-refractive layer and mainly distributing the hollow inorganic nanoparticles in the region of the low-refractive layer opposite to the interface, it is possible to achieve lower reflectance than the actual reflectance which could be obtained using the inorganic particles in the past.

In detail, the anti-reflective film may have average reflectance of 1.5% or less, 1.0% or less, 0.50% to 1.0%, 0.60% to 0.70%, or 0.62% to 0.67% in a visible light wavelength region of 380 nm to 780 nm.

Meanwhile, the first layer may have a thickness of 1 nm to 50 nm, 2 nm to 40 nm, or 3 nm to 30 nm, and the second layer may have a thickness of 5 nm to 300 nm, 10 nm to 200 nm, from 20 nm to 150 nm, from 25 nm to 120 nm, or from 30 nm to 100 nm.

The thicknesses of the first and second layers may also be confirmed by fitting the polarization ellipticity measured by ellipsometry using the Cauchy model represented by General Formula 1.

The solid inorganic nanoparticles are particles having a maximum diameter of 100 nm or less and a shape in which an empty space is not present in the insides thereof.

Further, the hollow inorganic nanoparticles are particles having a maximum diameter of 200 nm or less and a shape in which an empty space is present on surfaces and/or the insides thereof.

The solid inorganic nanoparticles may have a diameter of 5 to 100 nm, 1 to 50 nm, 5 to 30 nm, or 10 to 20 nm.

The hollow inorganic nanoparticles may have a diameter of 1 to 200 nm, 10 to 100 nm, 20 to 80 nm, or 40 to 70 nm.

The diameter of the solid inorganic nanoparticles and the hollow inorganic nanoparticles may mean the longest diameter of each of nanoparticles, which is identified on the cross-section.

Meanwhile, each of the solid inorganic nanoparticles and the hollow inorganic nanoparticles contains one or more reactive functional groups selected from the group consisting of a (meth)acrylate group, an epoxide group, a vinyl group, and a thiol group on a surface thereof.

As each of the solid inorganic nanoparticles and the hollow inorganic nanoparticles contains the above-mentioned reactive functional group on the surface thereof, the low-refractive layer may have a higher cross-linking density, and thus it is possible to secure further improved scratch resistance and anti-pollution properties.

In the antireflection film of the embodiment(s) described above, the first layer and the second layer included in the low refractive layer may have refractive indexes in different ranges.

More specifically, the first layer included in the low refraction layer may have a refractive index in a range of 1.420 to 1.600, 1.450 to 1.550, 1.480 to 1.520, or 1.491 to 1.511, at 550 nm.

In addition, the second layer included in the low refractive layer may have a refractive index in a range of 1.200 to 1.410, 1.210 to 1.400, or 1.211 to 1.375, at 550 nm.

The polarization ellipticity measured by ellipsometry and related data (Ellipsometry data ($\psi$, $\Delta$)) may be measured by a method and an apparatus generally known in the art.

The refractive index can be measured by a conventionally known method. For example, the refractive index can be determined by calculating the refractive index at 550 nm based on the elliptically polarized light and the Cauchy model measured at a wavelength of 380 nm to 1000 nm for each of the first layer and the second layer included in the low refractive layer Meanwhile, the low-refractive layer as described above may be manufactured from a photocurable coating composition containing a photopolymerizable compound, a fluorine-containing compound including a photoreactive functional group, the hollow inorganic nanoparticles, the solid inorganic nanoparticles, and a photoinitiator.

Therefore, the binder resin contained in the low-refractive layer contains a cross-linked (co)polymer between a (co)polymer of the photopolymerizable compound and the fluorine-containing compound including the photoreactive functional group.

The photopolymerizable compound contained in the photocurable coating composition according to the exemplary embodiment may form a substrate of the binder resin of the manufactured low-refractive layer. In detail, the photopolymerizable compound may include a monomer or oligomer including (meth)acrylate or a vinyl group. In more detail, the photopolymerizable compound may include a monomer or oligomer including at least one, at least two, or at least three (meth)acrylates or vinyl groups.

A specific example of the monomer or oligomer including (meth)acrylate may include: pentaerythritol tri(meth)acrylate, pentaerythritol tetra(meth)acrylate, dipentaerythritol penta(meth)acrylate, dipentaerythritol hexa(meth)acrylate, tripentaerythritol hepta(meth)acrylate, trilene diisocyanate, xylene diisocyanate, hexamethylene diisocyanate, trimethylolpropane tri(meth)acrylate, trimethylolpropane polyethoxy tri(meth)acrylate, trimethylolpropane trimethacrylate, ethylene glycol dimethacrylate, butanediol dimethacrylate, hexaethyl methacrylate, butyl methacrylate, or a mixture of two or more thereof; or an urethane modified acrylate oligomer, an epoxide acrylate oligomer, an etheracrylate oligomer, a dendritic acrylate oligomer, or a mixture of two or more thereof. Here, it is preferable that a molecular weight of the oligomer is 1000 to 10,000.

A specific example of the monomer or oligomer including the vinyl group may include divinyl benzene, styrene, or paramethylstyrene.

A content of the photopolymerizable compound in the photocurable coating composition is not particularly limited, but in consideration of mechanical properties and the like of a low-refractive layer or anti-reflective film to be finally manufactured, the content of the photopolymerizable compound may be 5 wt % to 80 wt % based on a solid component of the photocurable coating composition. The solid component of the photocurable coating composition is only a solid-state component of the photocurable coating composition excluding liquid-state components, for example, an organic solvent and the like, which may be selectively contained as described below.

Meanwhile, the photopolymerizable compound may further contain a fluorinated (meth)acrylate-based monomer or oligomer in addition to the above-mentioned monomer or oligomer. In the case in which the photopolymerizable compound further contains the fluorinated (meth)acrylate-based monomer or oligomer, a weight ratio of the fluorinated (meth)acrylate-based monomer or oligomer to the monomer or oligomer including the (meth)acrylate or vinyl group may be 0.1% to 10%.

A specific example of the fluorinated (meth)acrylate-based monomer or oligomer may include one or more selected from the group consisting of compounds represented by the following Chemical Formulas 11 to 15.

[Chemical Formula 11]

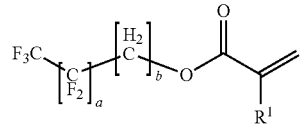

In Chemical Formula 11, $R^1$ is hydrogen or an alkyl group having 1 to 6 carbon atoms, a is an integer of 0 to 7, and b is an integer of 1 to 3.

[Chemical Formula 12]

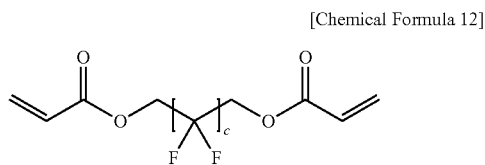

In Chemical Formula 12, c is an integer of 1 to 10.

[Chemical Formula 13]

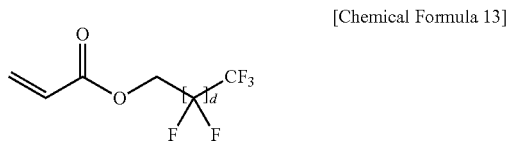

In Chemical Formula 13, d is an integer of 1 to 11.

[Chemical Formula 14]

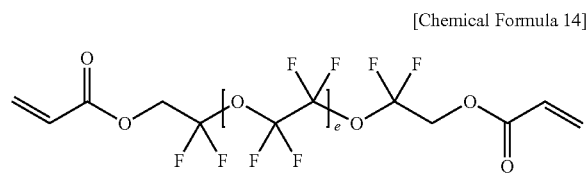

In Chemical Formula 14, e is an integer of 1 to 5.

[Chemical Formula 15]

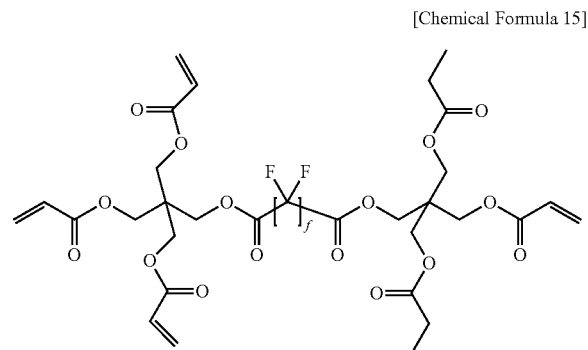

In Chemical Formula 15, f is an integer of 4 to 10.

Meanwhile, a moiety derived from the fluorine-containing compound including the photoreactive functional group may be contained in the low-refractive layer.

One or more photoreactive functional groups may be included or substituted in the fluorine-containing compound including the photoreactive functional group, wherein the photoreactive functional group is a functional group capable of participating in a polymerization reaction by light irradiation, for example, visible light irradiation or UV light irradiation. The photoreactive functional group may include various functional groups known to participate in a polymerization reaction by light irradiation, and a specific example thereof may include a (meth)acrylate group, an epoxide group, a vinyl group, or a thiol group.

Each of the fluorine-containing compounds including the photoreactive functional group may have a weight average molecular weight (weight average molecular weight measured by gel permeation chromatography (GPC) in terms of polystyrene) of 2000 to 200,000, and preferably 5000 to 100,000.

When the weight average molecular weight of the fluorine-containing compounds including the photoreactive functional group is excessively small, the fluorine-containing compounds in the photocurable coating composition may not be uniformly and effectively arranged on a surface, but are positioned inside the finally manufactured low-refractive layer such that the anti-pollution property of the surface of the low-refractive layer may be deteriorated, and mechanical properties such as entire strength, scratch resistance, and the like may be deteriorated due to a decrease in the cross-linking density of the low-refractive layer.

Further, when the weight average molecular weight of the fluorine-containing compounds including the photoreactive functional group is excessively large, compatibility with other components in the photocurable coating composition may be deteriorated, such that a haze of the finally manufactured low-refractive layer may be increased or the light transmittance thereof may be decreased, and strength of the low-refractive layer may also be deteriorated.

In detail, the fluorine-containing compound including the photoreactive functional group may be: i) an aliphatic compound or alicyclic compound in which one or more photoreactive functional groups are substituted, and at least one carbon atom is substituted with one or more fluorine atoms; ii) a heteroaliphatic compound or heteroalicyclic compound in which one or more photoreactive functional groups are substituted, at least one hydrogen atom is substituted with a fluorine atom, and one or more carbon atoms are substituted with a silicon atom; iii) a polydialkylsiloxane-based polymer (for example, a polydimethylsiloxane-based polymer) in which one or more photoreactive functional groups are substituted, and at least one silicon atom is substituted with one or more fluorine atoms; iv) a polyether compound in which one or more photoreactive functional groups are substituted, and at least one hydrogen atom is substituted with a fluorine atom; or a mixture of two or more of i) to iv) or a copolymer thereof.

The photocurable coating composition may contain 20 to 300 parts by weight of the fluorine-containing compound including the photoreactive functional group, based on 100 parts by weight of the photopolymerizable compound.

When an amount of the fluorine-containing compound including the photoreactive functional group is excessively large as compared to the photopolymerizable compound, a coating property of the photocurable coating composition according to the exemplary embodiment may be deteriorated, or the low-refractive layer obtained from the photocurable coating composition may not have sufficient durability or scratch resistance. Further, when the amount of the fluorine-containing compound including the photoreactive functional group is excessively small as compared to the photopolymerizable compound, the low-refractive layer obtained from the photocurable coating composition may not have sufficient mechanical properties such as the anti-pollution property, scratch resistance, or the like.

The fluorine-containing compound including the photoreactive functional group may further contain silicon or a silicon compound. That is, the fluorine-containing compound including the photoreactive functional group may selectively contain silicon or the silicon compound therein. More specifically, a content of silicon in the fluorine-containing compound including the photoreactive functional group may be 0.1 wt % to 20 wt %.

The silicon contained in the fluorine-containing compound including the photoreactive functional group may improve compatibility with other components contained in the photocurable coating composition according to the exemplary embodiment, and thus the silicon may serve to increase transparency by preventing haze generation in the finally manufacture refractive layer. Meanwhile, when the content of silicon in the fluorine-containing compound including the photoreactive functional group is excessively high, compatibility between other ingredients contained in the photocurable coating composition and the fluorine-containing compound may be rather deteriorated, and thus the finally manufactured low-refractive layer or anti-reflective film may not have sufficient light transmittance or anti-reflection performance, and the anti-pollution property of the surface may also be deteriorated.

The low-refractive layer may contain 10 to 400 parts by weight of the hollow inorganic nanoparticles and 10 to 400 parts by weight of the solid inorganic nanoparticles, based on 100 parts by weight of the (co)polymer of the photopolymerizable compound.

In the case in which the contents of the hollow inorganic nanoparticles and the solid inorganic nanoparticles in the low-refractive layer are excessively high, in a manufacturing process of the low-refractive layer, the hollow inorganic nanoparticles and the solid inorganic nanoparticles may not be sufficiently phase-separated, but mixedly exist, such that the reflectance may be increased, and the surface may become excessively uneven such that the anti-pollution property may be deteriorated. Further, in the case in which the contents of the hollow inorganic nanoparticles and the solid inorganic nanoparticles in the low-refractive layer are excessively low, it may be difficult to allow the solid inorganic nanoparticles to be mainly positioned in the region close to the interface between the hard coating layer and the low-refractive layer, and the reflectance of the low-refractive layer may be significantly increased.

The low-refractive layer may have a thickness of 1 nm to 300 nm, or 50 nm to 200 nm.

Meanwhile, as the hard coating layer, a hard coating layer generally known in the art may be used without limitation.

As an example of the hard coating layer, there is a hard coating layer containing a binder resin containing a photocurable resin, and organic or inorganic fine particles dispersed in the binder resin.

The photocurable resin contained in the hard coating layer, which is a polymer of a photopolymerizable compound capable of causing a polymerization reaction when light such as UV light or the like is irradiated, may be a photocurable resin generally used in the art. In detail, the photocurable resin may include one or more selected from the group consisting of the reactive acrylate oligomer group consisting of an urethane acrylate oligomer, an epoxide acrylate oligomer, polyester acrylate, and polyether acrylate; and the multi-functional acrylate monomer group consisting of dipentaerythritol hexaacrylate, dipentaerythritol hydroxy pentaacrylate, pentaerythritol tetraacrylate, pentaerythritol triacrylate, trimethylene propyl triacrylate, propoxylated glycerol triacrylate, trimethylpropane ethoxy triacrylate, 1,6-dihexanediol acrylate, propoxylated glycero triacrylate, tripropylene glycol diacrylate, and ethylene glycol diacrylate.

A particle diameter of the organic or inorganic fine particles is not specifically limited, but for example, the organic fine particles may have a particle diameter of 1 to 10 μm, and the inorganic fine particles may have a particle diameter of 1 nm to 500 nm, or 1 nm to 300 nm.

The particle diameter of the organic or inorganic fine particles may be defined as a volume average particle diameter.

Specific examples of the organic or inorganic fine particles contained in the hard coating layer are not limited, but may include, for example, organic fine particles made of an acrylic resin, a styrene-based resin, an epoxide resin, and a nylon resin, or inorganic fine particles made of silicon oxide, titanium dioxide, indium oxide, tin oxide, zirconium oxide, and zinc oxide.

The binder resin of the hard coating layer further comprises a high-molecular weight (co)polymer having weight average molecular weight of 10,000 or more.

The hard coating film may be formed from an anti-glare coating composition containing organic or inorganic fine particles, a photocurable resin, a photoinitiator, and a high-molecular weight (co)polymer having a weight average molecular weight of 10,000 or more.

Meanwhile, as another example of the hard coating film, there is a hard coating film containing a binder resin including a photocurable resin, and an antistatic agent dispersed in the binder resin.

The photocurable resin contained in the hard coating layer, which is a polymer of a photopolymerizable compound capable of causing a polymerization reaction when light such as UV light or the like is irradiated, may be a photocurable resin generally used in the art. However, preferably, the photopolymerizable compound may be a multi-functional (meth)acrylate-based monomer or oligomer. Here, in view of securing physical properties of the hard coating layer, the number of (meth)acrylate-based functional groups is 2 to 10, preferably 2 to 8, and more preferably 2 to 7. More preferably, the photopolymerizable compound may be one or more selected from the group consisting of pentaerythritol tri(meth)acrylate, pentaerythritol tetra(meth)acrylate, dipentaerythritol penta(meth)acrylate, dipentaerythritol hexa(meth)acrylate, dipentaerythritol hepta(meth)acrylate, tripentaerythritol hepta(meth)acrylate, trilene diisocyanate, xylene diisocyanate, hexamethylene diisocyanate, trimethylolpropane tri(meth)acrylate, and trimethylolpropane polyethoxy tri(meth)acrylate.

The antistatic agent may be a quaternary ammonium salt compound; a pyridinium salt; a cationic compound having 1 to 3 amino groups; an anionic compound such as a sulfonic acid-based compound, a sulfuric acid ester-based compound, a phosphoric acid ester-based compound, a phosphonic acid-based compound, or the like; an amphoteric compound such as an amino acid-based or amino sulfuric acid ester-based compound, or the like; a non-ionic compound such as an imino alcohol-based compound, a glycerine-based compound, a polyethylene glycol-based compound, or the like; an organic metal compound such as metal alkoxide compound containing tin, titanium, etc., or the like; a metal chelate compound such as an acetylacetonate salt of the organic metal compound, or the like; a reaction product or polymer compound of two or more thereof; or a mixture of two or more thereof. Here, the quaternary ammonium salt compound may be a compound having one or more quaternary ammonium salt groups in a molecule, and a low-molecular weight quaternary ammonium salt compound or a high-molecular weight quaternary ammonium salt compound may be used without limitation.

Further, as the antistatic agent, a conductive polymer and metal oxide fine particles may also be used. An example of the conductive polymer includes aromatic conjugated poly (paraphenylene), heterocyclic conjugated polypyrrole, polythiophene, aliphatic conjugated polyacetylene, heteroatomcontaining conjugated polyaniline, and a mixed type of conjugated poly(phenylenevinylene), a double chain conjugated compound, which is a conjugated compound having a plurality of conjugated chains in a molecule, a conductive complex in which a conjugated polymer chain is grafted to or block-copolymerized with a saturated polymer, and the like. Further, the metal oxide fine particles may be made of zinc oxide, antimony oxide, tin oxide, cerium oxide, indium tin oxide, indium oxide, aluminum oxide, tin oxide doped with antimony, zinc oxide doped with aluminum, or the like.

The hard coating film containing the binder resin including the photocurable resin, and the antistatic agent dispersed in the binder resin, may further contain one or more compounds selected from the group consisting of an alkoxy silane-based oligomer and a metal alkoxide-based oligomer.

The alkoxy silane-based compound may be an alkoxy silane-based compound generally used in the art, but may preferably be one or more compounds selected from the group consisting of tetramethoxysilane, tetraethoxysilane, tetraisopropoxysilane, methyltrimethoxysilane, methyltriethoxysilane, methacryloxypropyltrimethoxysilane, glycidoxypropyl trimethoxysilane, and glycidoxypropyl triethoxysilane.

Further, the metal alkoxide-based oligomer may be prepared by a sol-gel reaction of a composition containing a metal alkoxide-based compound and water. The sol-gel reaction may be carried out by a method equivalent to a preparation method of the alkoxy silane-based oligomer described above.

However, since the metal alkoxide-based compound may violently react with water, the sol-gel reaction may be carried out by diluting the metal alkoxide-based compound in an organic solvent and then slowly dripping water thereinto. Here, it is preferable that a molar ratio (based on a metal ions) of the metal alkoxide compound to water is adjusted in a range of 3 to 170 in consideration of reaction efficiency, or the like.

Here, the metal alkoxide-based compound may be one or more compounds selected from the group consisting of titanium tetra-isopropoxide, zirconium isopropoxide, and aluminum isopropoxide.

The hard coating layer may have a thickness of 0.1 μm to 100 μm.

The anti-reflective film may further include a substrate bonded to the other surface of the hard coating layer. A specific kind or thickness of the substrate is not particularly limited, but a substrate known to be used for manufacturing a low-refractive layer or anti-reflective film may be used without limitation.

The anti-reflective film according to the exemplary embodiment of the present invention may be manufactured by a manufacturing method of an anti-reflective film, including: applying a resin composition for forming a low-refractive layer, containing a photopolymerizable compound or a (co)polymer thereof, a fluorine-containing compound including a photoreactive functional group, a photoinitiator, hollow inorganic nanoparticles, and solid inorganic nanoparticles on a hard coating layer and drying the applied resin composition at a temperature of 35□ to 100□; and photocuring the dried resin composition.

More specifically, in the anti-reflective film manufactured by the manufacturing method of an anti-reflective film described above, the hollow inorganic nanoparticles and the solid inorganic nanoparticles are distributed in the low-refractive layer so as to be distinguished from each other, such that the anti-reflective film may have low reflectance and high light transmittance and simultaneously implement high scratch resistance and anti-pollution properties.

In more detail, in the anti-reflective film manufactured by the manufacturing method of an anti-reflective film, the low-refractive layer may include a first layer containing at least 70 vol % of the entire solid inorganic nanoparticles and a second layer containing at least 70 vol % of the entire hollow inorganic nanoparticles, wherein the first layer may be positioned to be closer to an interface between the hard coating layer and the low-refractive layer than the second layer.

The low-refractive layer may be formed by applying the resin composition for forming a low-refractive layer, containing the photopolymerizable compound or the (co)polymer thereof, the fluorine-containing compound including the photoreactive functional group, the photoinitiator, the hollow inorganic nanoparticles, and the solid inorganic nanoparticles on the hard coating layer, and drying the applied resin composition at a temperature of 35° C. to 100° C. or 40° C. to 80° C.

When a drying temperature of the resin composition for forming a low-refractive layer applied on the hard coating layer is lower than 35° C., an anti-pollution property of the formed low-refractive layer may be significantly deteriorated. Further, when the drying temperature of the resin composition for forming a low-refractive layer applied on the hard coating layer is higher than 100° C., in a manufacturing process of the low-refractive layer, the hollow inorganic nanoparticles and the solid inorganic nanoparticles may not be sufficiently phase-separated, but mixedly exist, such that the scratch resistance and anti-pollution properties of the low-refractive layer may be deteriorated, and the reflectance may also be significantly increased.

The low-refractive layer having the above-mentioned characteristics may be formed by adjusting a density difference between the solid inorganic nanoparticles and the hollow inorganic nanoparticles in addition to the drying temperature during a drying process of the resin composition for forming a low-refractive layer applied on the hard coating layer. The density of the solid inorganic nanoparticles may be at least 0.50 $g/cm^3$ higher than that of the hollow inorganic nanoparticles, and due to this density difference, the solid inorganic nanoparticles may be positioned in the low-refractive layer formed on the hard coating layer to be closer to the hard coating layer.

In detail, the solid inorganic nanoparticles may have a density of 2.00 $g/cm^3$ to 4.00 $g/cm^3$ and the hollow inorganic nanoparticles may have a density of 1.50 $g/cm^3$ to 3.50 $g/cm^3$.

The drying of the resin composition for forming a low-refractive layer, applied on the hard coating layer at a temperature of 35° C. to 100° C., may be performed for 10 seconds to 5 minutes, or 30 seconds to 4 minutes.

When a drying time is excessively short, a phase separation phenomenon between the hollow inorganic nanoparticles and the solid inorganic nanoparticles described above may not sufficiently occur. On the contrary, when the drying time is excessively long, the formed low-refractive layer may infiltrate into the hard coating layer.

The low-refractive layer may be manufactured from a photocurable coating composition containing a photopolymerizable compound or a (co)polymer thereof, a fluorine-containing compound including a photoreactive functional group, the hollow inorganic nanoparticles, the solid inorganic nanoparticles, and a photoinitiator.

The low-refractive layer may be obtained by photocuring the resultant obtained by applying the photocurable coating composition on a predetermined substrate. A specific kind or thickness of the substrate is not particularly limited, but a substrate known to be used for manufacturing a low-refractive layer or anti-reflective film may be used without limitation.

A method and an apparatus generally used to apply the photocurable coating composition may be used without particular limitation. For example, a bar coating method such as a Meyer bar coating method or the like, a gravure coating method, a 2-roll reverse coating method, a vacuum slot die coating method, a 2-roll coating method, or the like, may be used.

The low-refractive layer may have a thickness of 1 nm to 300 nm, or 50 nm to 200 nm. Accordingly, the thickness of the photocurable coating composition applied on the predetermined substrate may be about 1 nm to 300 nm, or 50 nm to 200 nm.

Accordingly, the thickness of the photocurable coating composition applied on the predetermined substrate may be about 1 nm to 300 nm, or 50 nm to 200 nm.

In the photocuring of the photocurable coating composition, UV light or visible light having a wavelength of 200 to 400 nm may be irradiated, and at the time of irradiation, it is preferable that an exposure amount is 100 to 4000 mJ/cm$^2$. An exposure time is not particularly limited, but may be suitably changed depending on a used exposure device, a wavelength of the irradiated light, or the exposure amount.

Further, in the photocuring of the photocurable coating composition, nitrogen purging or the like may be performed in order to apply a nitrogen atmosphere condition.

Detailed contents of the photopolymerizable compound, the hollow inorganic nanoparticles, the solid inorganic nanoparticles, and the fluorine-containing compound including the photo-reactive functional group include those in the anti-reflective film according to the exemplary embodiment described above.

Each of the hollow inorganic nanoparticles and the solid inorganic nanoparticles may be contained in the composition in a colloidal phase in which they are dispersed in a predetermined dispersion medium. The colloidal phase containing each of the hollow inorganic nanoparticles and the solid inorganic nanoparticles may contain an organic solvent as the dispersion medium.

A content of the hollow inorganic nanoparticles and a content of the solid inorganic nanoparticles in the colloidal phase may be determined in consideration of a content range of the hollow inorganic nanoparticles and a content range of the solid inorganic nanoparticles in the photocurable coating composition, a viscosity of the photocurable coating composition, or the like. For example, the solid content of the hollow inorganic nanoparticles and the solid content of the solid inorganic nanoparticles in the colloidal phase may be 5 wt % to 60 wt %, respectively.

An example of the organic solvent used as the dispersion medium may include: alcohols such as methanol, isopropyl alcohol, ethylene glycol, butanol, and the like; ketones such as methylethylketone, methylisobutylketone, and the like; aromatic hydrocarbons such as toluene, xylene, and the like; amides such as dimethylformamide, dimethylacetamide, N-methylpyrrolidone, and the like; esters such as ethyl acetate, butyl acetate, gamma-butyrolactone, and the like; ethers such as tetrahydrofuran, 1,4-dioxane, and the like; or a mixture thereof.

As the photoinitiator, any compound may be used without particular limitation as long as it is known to be usable in a photocurable resin composition. More specifically, a benzophenone-based compound, an acetophenone-based compound, a biimidazole-based compound, a triazine-based compound, an oxime-based compound, or a mixture of two or more thereof may be used.

The photoinitiator may be used in a content of 1 to 100 parts by weight based on 100 parts by weight of the photopolymerizable compound. When the content of the photoinitiator is excessively low, some materials that are not cured in the photocuring of the photocurable coating composition may remain. When the content of the photoinitiator is excessively high, an unreacted initiator may remain as an impurity or a cross-linking density may be decreased, such that mechanical properties of a manufactured film may be deteriorated, or reflectance thereof may be significantly increased.

The photocurable coating composition may further contain an organic solvent.

A non-restrictive example of the organic solvent may include ketones, alcohols, acetates, and ethers, or a mixture of two or more thereof.

A specific example of the organic solvent as described above may include: the ketones such as methylethylketone, methylisobutylketone, acetylacetone, isobutylketone, or the like; the alcohols such as methanol, ethanol, diacetone alcohol, n-propanol, i-propanol, n-butanol, i-butanol, t-butanol, or the like; the acetates such as ethylacetate, i-propylacetate, polyethylene glycol monomethylether acetate, or the like; the ethers such as tetrahydrofuran, propylene glycol monomethylether, or the like; or a mixture of two or more thereof.

The organic solvent may be added at the time of mixing each of the components contained in the photocurable coating composition, or may be added in a state in which each of the components is dispersed in or mixed with the organic solvent, such that the organic solvent may be contained in the photocurable coating composition. When a content of the organic solvent in the photocurable coating composition is excessively low, flowability of the photocurable coating composition may be deteriorated, such that defects such as formation of a stripe pattern or the like may occur in the finally manufactured film. Further, when the organic solvent is excessively added, a solid content may be decreased, such that coating and film formation may not be sufficiently performed, and thus physical properties or surface characteristics of the film may be deteriorated, and a defect may occur in the drying and curing processes. Therefore, the photocurable coating composition may contain the organic solvent so that a total concentration of the solid components contained therein is 1 wt % to 50 wt %, or 2 wt % to 20 wt %.

A material of the hard coating layer is not particularly limited as long as it is known to be usable in an anti-reflective film.

In detail, the manufacturing method of an anti-reflective film may further include applying a polymer resin composition for forming a hard coating layer, containing a photopolymerizable compound or a (co)polymer thereof, a photoinitiator, and an antistatic agent on a substrate and photocuring the applied polymer resin composition, and the hard coating layer may be formed by this step.

The components used to form the hard coating layer are the same as those in the anti-reflective film according to the present invention described above.

The polymer resin composition for forming a hard coating layer may further contain one or more compounds selected from the group consisting of an alkoxy silane-based oligomer and a metal alkoxide-based oligomer.

A method and an apparatus generally used to apply the polymer resin composition for forming a hard coating layer may be used without particular limitation. For example, a bar coating method such as a Meyer bar coating method or the like, a gravure coating method, a 2-roll reverse coating method, a vacuum slot die coating method, a 2-roll coating method, or the like, may be used.

In the photocuring of the polymer resin composition for forming a hard coating layer, UV light or visible light having a wavelength of 200 to 400 nm may be irradiated, and at the time of irradiation, it is preferable that an exposure amount is 100 to 4000 mJ/cm$^2$. An exposure time is not particularly limited, but may be suitably changed depending on a used exposure device, a wavelength of the irradiated light, or the exposure amount. Further, in the photocuring of the polymer resin composition for forming a hard coating layer, nitrogen purging or the like may be performed in order to apply a nitrogen atmosphere condition.

Advantageous Effects

According to the present invention, the anti-reflective film capable of having low reflectance and high light transmittance, simultaneously implementing high scratch resistance and anti-pollution properties, and enhancing sharpness of a screen of a display device, and a manufacturing method thereof, may be provided.

BRIEF DESCRIPTION OF THE DRAWINGS

FIG. 1 is a transmission electron microscope (TEM) photograph of a cross-section of an anti-reflective film in Example 1.

FIG. 2 is a TEM photograph of a cross-section of an anti-reflective film in Example 2.

FIG. 3 is a TEM photograph of a cross-section of an anti-reflective film in Example 3.

FIG. 4 is a TEM photograph of a cross-section of an anti-reflective film in Example 4.

FIG. 5 is a TEM photograph of a cross-section of an anti-reflective film in Example 5.

FIG. 6 is a TEM photograph of a cross-section of an anti-reflective film in Example 6.

FIG. 7 is a TEM photograph of a cross-section of an anti-reflective film in Comparative Example 1.

FIG. 8 is a TEM photograph of a cross-section of an anti-reflective film in Comparative Example 2.

DETAILED DESCRIPTION OF THE EMBODIMENTS

The present invention will be described in more detail through the following examples. However, the following examples are only to exemplify the present invention, and contents of the present invention are not limited by the following examples.

PREPARATION EXAMPLE

Preparation Example: Manufacturing of Hard Coating Film

A salt-type antistatic hard coating solution (KYOEISHA Chemical Co., Ltd., solid content: 50 wt %, product name: LJD-1000) was coated on a triacetyl cellulose film using a #10 Mayer bar, dried at 90□ for 1 minute, and irradiated with UV light (150 mJ/cm$^2$), thereby manufacturing a hard coating film having a thickness of about 5 μm.

Examples 1 to 5: Manufacturing of Anti-Reflective Film

Examples 1 to 4

(1) Preparation of Photocurable Coating Composition for Forming Low-Refractive Layer Based on 100 parts by weight of pentaerythritol triacrylate (PETA), 281 parts by weight of hollow silica nanoparticles (diameter: about 50 to 60 nm, density: 1.96 g/cm$^3$, JGC Catalyst and Chemicals), 63 parts by weight of solid silica nanoparticles (diameter: about 12 nm, density: 2.65 g/cm$^3$), 131 parts by weight of a first fluorine-containing compound (X-71-1203M, Shin-Etsu), 19 parts by weight of a second fluorine-containing compound (RS-537, DIC), and 31 parts by weight of an initiator (Irgacure 127, Ciba) were diluted in a solvent in which methyl isobutyl ketone (MIBK), diacetone alcohol (DAA), and isopropyl alcohol were mixed at a weight ratio of 3:3:4 so that a solid content was 3 wt %.

(2) Manufacturing of Low-Refractive Layer and Anti-Reflective Film

The photocurable coating composition obtained above was coated on the hard coating film in the preparation example using a #4 Mayer bar so as to have a thickness of about 120 nm, and dried and cured at a temperature illustrated in the following Table 1 for a time illustrated in the following Table 1. At the time of curing, the dried coating resultant was irradiated with UV light (252 mJ/cm$^2$) under nitrogen purging.

Example 5

(1) Preparation of Photocurable Coating Composition for Forming Low-Refractive Layer Based on 100 parts by weight of trimethylolpropane triacrylate (TMPTA), 268 parts by weight of hollow silica nanoparticles (diameter: about 50 to 60 nm, density: 1.96 g/cm$^3$, JGC Catalyst and Chemicals), 55 parts by weight of solid silica nanoparticles (diameter: about 12 nm, density: 2.65 g/cm$^3$), 144 parts by weight of a first fluorine-containing compound (X-71-1203M, Shin-Etsu), 21 parts by weight of a second fluorine-containing compound (RS-537, DIC), and 31 parts by weight of an initiator (Irgacure 127, Ciba) were diluted in a methyl isobutyl ketone (MIBK) solvent so that a solid content was 3 wt %.

(2) Manufacturing of Low-Refractive Layer and Anti-Reflective Film

The photocurable coating composition obtained above was coated on the hard coating film in the preparation example using a #4 Mayer bar so as to have a thickness of about 110 to 120 nm, and dried and cured at a temperature illustrated in the following Table 1 for a time illustrated in the following Table 1. At the time of curing, the dried coating resultant was irradiated with UV light (252 mJ/cm$^2$) under nitrogen purging.

TABLE 1

|  | Drying Temperature | Drying Time |
| --- | --- | --- |
| Example 1 | 40° C. | 1 min |
| Example 2 | 60° C. | 1 min |
| Example 3 | 80° C. | 1 min |
| Example 4 | 60° C. | 2 min |
| Example 5 | 60° C. | 3 min |

Example 6

(1) Preparation of Hard Coating Later (HD2)

30 g of pentaerythritol triacrylate, 2.5 g of a high molecular weight copolymer (BEAMSET 371, Arakawa Co. Ltd., Epoxy Acrylate, molecular weight 40,000), 20 g of methylethylketone, and 0.5 g of a leveling agent (Tego wet 270) were uniformly mixed, and then 2 g of an acryl-styrene copolymer (volume average particle diameter: 2 μm, Manufacturing Company: Sekisui Plastic) with a refractive index of 1.525 was added as fine particles to prepare a hard coating composition.

The above-obtained hard coating composition was coated on a triacetyl cellulose film with a #10 Mayer bar and dried at 90° C. for 1 minute. The dried coating was irradiated by UV at 150 mJ/cm² to prepare a hard coating layer with a thickness of 5 μm.

(2) Preparation of a Low Refractive Layer and an Anti-Reflective Film

Based on 100 parts by weight of pentaerythritol triacrylate (PETA), 135 parts by weight of hollow silica nanoparticles (diameter: about 50 to 60 nm, density: 1.96 g/cm³, manufactured by JSC Catalysts and Chemicals Ltd.), 88 parts by weight of solid silica nanoparticles (diameter: about 12 nm, density: 2.65 g/cm³), 38 parts by weight of a first fluorine-containing compound (X-71-1203M, ShinEtsu Chemical Co., Ltd.), 11 parts by weight of a second fluorine-containing compound (RS-537, DIC Corporation), and 7 parts by weight of an initiator (Irgacure 127, Ciba Corporation) were diluted in a mixed solvent of MIBK (methyl isobutyl ketone):diacetone alcohol (DAA):isopropyl alcohol at a weight ratio of 3:3:4 such that the solid concentration became 3 wt %, thus preparing a photocurable coating composition for forming a low refractive layer.

On the above-prepared hard coating film (HD2), the above obtained photocurable coating composition for forming a low refractive layer was coated to a thickness of about 110 to 120 nm with a #4 Mayer bar, and dried and cured at a temperature of 60° C. for 1 minute. During the curing, UV at 252 mJ/cm² was irradiated to the dried coating under nitrogen purging.

Comparative Example: Manufacturing of Anti-Reflective Film

Comparative Example 1

An anti-reflective film was manufactured by the same method as in Example 1, except for applying the photocurable coating composition for forming a low-refractive layer and drying the applied photocurable coating composition at room temperature (25□).

Comparative Example 2

A photocurable coating composition for forming a low-refractive layer was prepared by the same method as in Example 1, except for replacing 63 parts by weight of the solid silica nanoparticles used in Example 1 with 63 parts by weight of pentaerythritol triacrylate (PETA), and an anti-reflective film was manufactured by the same method as in Example 1.

Experimental Example: Measurement of Physical Properties of Anti-Reflective Film Experiments composed of the following categories were performed on the anti-reflective films obtained in the examples and comparative examples.

1. Measurement of Average Reflectance of Anti-Reflective Film

Average reflectances of the anti-reflective films obtained in the examples and comparative examples in a visible light region (380 to 780 nm) were measured using Solidspec 3700 (SHIMADZU).

2. Measurement of Anti-Pollution Property

An anti-pollution property was measured by drawing a straight line having a length of 5 cm on surfaces of the anti-reflective films obtained in the examples and comparative examples using a black name pen and confirming the number of scrubbing actions required for erasing the straight line at the time of scrubbing the antireflective film with a wiper.

Measurement Standard

○: The number of rubbing actions required for erasing the straight line was 10 or less.

Δ: The number of rubbing actions required for erasing the straight line was 11 to 20.

X: The number of rubbing actions required for erasing the straight line was more than 20.

3. Measurement of Scratch Resistance

Steel wool was rubbed on surfaces of the anti-reflective films obtained in the examples and comparative examples under load while reciprocating the anti-reflective film at a rate of 27 rpm 10 times. A maximum load at which the number of scratches (1 cm or less) observed by the naked eye was 1 or less was measured.

4. Confirmation of Phase-Separation

When 70 vol % of the entire used solid inorganic nanoparticles (solid silica nanoparticles) was present within a distance of 30 nm from the hard coating layer in cross-sections of the anti-reflective films in FIGS. 1 to 7, it was determined that phase separation occurred.

5. Ellipsometry Measurement

Polarization ellipticities of the low-refractive layers obtained in the examples and comparative examples, respectively, were measured using ellipsometry.

In detail, linear polarization of each of the low-refractive layers obtained in the examples and comparative examples was measured in a wavelength range of 380 nm to 1000 nm at an incident angle of 70° using an ellipsometer (J. A. Woollam Co. M-2000). The measured linear polarization data (ellipsometry data ($\psi$, $\Delta$)) were fitted for the first and second layers (Layer 1 and Layer 2) of the low-refractive layer using Complete EASE software and a Cauchy model represented by the following General Equation 1 so that MSE was 3 or less.

$$n(\lambda) = A + \frac{B}{\lambda^2} + \frac{C}{\lambda^4} \qquad \text{[General Equation 1]}$$

In General Equation 1, $n(\lambda)$ is a refractive index at a wavelength of $\lambda$, $\lambda$ is in a range of 300 nm to 1800 nm, and A, B, and C are Cauchy parameters.

6. Measurement of Refractive Index

The refractive index at 550 nm was calculated using elliptically polarized light and a Cauchy model measured at a wavelength of 380 nm to 1000 nm for each of the first layer and the second layer included in the low refractive index layer obtained in the above examples.

TABLE 2

|  |  | Example 1 | Example 2 | Example 3 | Example 4 | Example 5 | Example 6 | Comparative Example 1 | Comparative Example 2 |
|---|---|---|---|---|---|---|---|---|---|
| Average Reflectance (%) | | 0.63 | 0.62 | 0.67 | 0.64 | 0.65 | 0.67 | 0.78 | 0.66 |
| Scratch Resistance (g) | | 500 | 500 | 500 | 500 | 500 | 500 | 150 | 50 |
| Anti-pollution property | | O | O | O | O | O | O | X | X |
| Phase Separation | | O | O | O | O | O | O | X | X |
| Ellipsometry measurment | | | | | | | | | |
| Layer 1 | A | 1.502 | 1.505 | 1.498 | 1.491 | 1.511 | 1.505 | 1.25 | 1.206 |
|  | B | 0.00351 | 0.00464 | 0.00311 | 0.00573 | 0.001924 | 0.00316 | 0.00192 | 0.07931 |
|  | C | $4.1280 * 10^{-4}$ | $3.4882 * 10^{-4}$ | $4.1352 * 10^{-4}$ | $3.9821 * 10^{-4}$ | $2.6729 * 10^{-4}$ | 0 | 0.003 | −0.004 |
| Layer 2 | A | 1.35 | 1.349 | 1.321 | 1.346 | 1.211 | 1.375 | 1.33 | 1.32 |
|  | B | 0.00513 | 0.00304 | 0.00312 | 0 | 0.00253 | 0.00178 | 0.00786 | 0.00040374 |
|  | C | $2.5364 * 10^{-4}$ | 0 | $4.1280 * 10^{-4}$ | $4.8685 * 10^{-4}$ | $1.6421 * 10^{-4}$ | $1.2131 * 10^{-5}$ | 0.000953 | 0.000782 |

TABLE 3

| Refractive index | Example 1 | Example 2 | Example 3 | Example 4 | Example 5 | Example 6 |
|---|---|---|---|---|---|---|
| Layer 1 | 1.502 | 1.505 | 1.498 | 1.491 | 1.511 | 1.505 |
| Layer 2 | 1.35 | 1.349 | 1.321 | 1.346 | 1.211 | 1.375 |

As illustrated in FIGS. 1 to 6, it was confirmed that in the low-refractive layers of the anti-reflective films in Examples 1 to 6, phase separation between the hollow inorganic nanoparticles and the solid inorganic nanoparticles occurred.

More specifically, as can be seen from the analysis results of FIGS. 1 to 6, it was confirmed that the low-refractive layer included a first layer containing at least 70 vol % of the entire solid inorganic nanoparticles and a second layer containing at least 70 vol % of the entire hollow inorganic nanoparticles, most of the solid inorganic nanoparticles were present and concentrated toward an interface between the hard coating layer and the low-refractive layer of the anti-reflective film, and most of the hollow inorganic nanoparticles were present and concentrated in a region far from the hard coating layer. Accordingly, the first layer containing at least 70% by volume of the total solid inorganic nanoparticles is located within 50% of the total thickness of the low refractive layer from the interface between the hard coating layer and low-refractive layer.

In addition, at the time of fitting polarization ellipticity measured by ellipsometry for the second layer included in the low-refractive layer using the Cauchy model represented by General Equation 1, the second layer satisfied the following conditions: A was 1.0 to 1.50, B was 0 to 0.007, and C was 0 to $1*10^{-3}$. In addition, at the time of fitting polarization ellipticity measured by ellipsometry for the first layer included in the low-refractive layer using the Cauchy model represented by General Equation 1, the first layer satisfied the following conditions: A was 1.0 to 1.65, B was 0.0010 to 0.0350, and C was 0 to $1*10^{-3}$.

In addition, as illustrated in Table 2, it was confirmed that the anti-reflective films in Examples may have a low reflectance of 0.70% or less in the visible light region and simultaneously implement high scratch resistance and anti-pollution property as illustrated in Table 2.

In addition, as shown in Table 3, the first layer and the second layer included in the low refraction layer of the examples exhibit different refractive indexes. Specifically, it was confirmed that the first layer of the low refraction layer has a refractive index of 1.420 or more and the second layer of the low refraction layer exhibited a refractive index of 1.400 or less.

On the contrary, as illustrated in FIGS. 6 and 7, it was confirmed that in the low-refractive layers of the anti-reflective films in Comparative Examples 1 and 2, the hollow inorganic nanoparticles and the solid inorganic nanoparticles were not phase-separated, but mixedly existed.

Further, it was confirmed that in the anti-reflective films in Comparative Examples 1 and 2, at the time of fitting the polarization ellipticity measured by ellipsometry using the Cauchy model represented by General Equation 1, measurement results and fitting results by the Cauchy model were in a different range from those in the anti-reflective films in Examples, and the anti-reflective films had low scratch resistance and anti-pollution property while having a relatively high reflectance.

What is claimed is:

1. An anti-reflective film comprising: a hard coating layer and a low-refractive layer, wherein the low-refractive layer contains hollow organic nanoparticles and solid inorganic nanoparticles that are dispersed in a binder resin, wherein the hollow inorganic particles are in a higher amount by weight than the solid inorganic particles
    wherein the low-refractive layer includes a first layer containing at least 70 vol % of the total volume of solid inorganic nanoparticles dispersed in the binder resin and a second layer containing at least 70 vol % of the total volume of hollow inorganic nanoparticles dispersed in the binder resin, and
    wherein the second layer has polarization ellipticity measured by ellipsometry using a Cauchy model represented by the following General Equation 1 in which A is 1.0 to 1.50, B is 0 to 0.007, and C is 0 to $1*10^{-3}$:

$$n(\lambda) = A + \frac{B}{\lambda^2} + \frac{C}{\lambda^4} \quad \text{[General Equation 1]}$$

in General Equation 1, n(λ) is a refractive index at a wavelength of λ, λ is in a range of 300 nm to 1800 nm, and A, B, and C are Cauchy parameters.

2. The anti-reflective film according to claim 1,
wherein the polarization ellipticity measured by ellipsometry is determined by measuring linear polarization in a wavelength range of 380 nm to 1000 nm at an incident angle of 70°.

3. The anti-reflective film according to claim 1, wherein the first layer has polarization ellipticity measured by ellipsometry using the Cauchy model represented by General Equation 1, in which A is 1.0 to 1.65, B is 0.0010 to 0.0350, and C is 0 to $1*10^{-3}$:

$$n(\lambda) = A + \frac{B}{\lambda^2} + \frac{C}{\lambda^4} \qquad \text{[General Equation 1]}$$

In General Equation 1, $n(\lambda)$ is a refractive index at a wavelength of $\lambda$, $\lambda$ is in a range of 300 nm to 1800 nm, and A, B, and C are Cauchy parameters.

4. The anti-reflective film according to claim 1,
wherein the first layer is positioned closer to the interface between the hard coating layer and the low-refractive layer than the second layer.

5. The anti-reflective film according to claim 1,
wherein the first layer containing at least 70 vol % of the entire solid inorganic nanoparticles is located within 50% of the total thickness of the low-refractive layer from the interface between the hard coating layer and the low-refractive layer.

6. The anti-reflective film according to claim 1,
wherein the first layer has a thickness of 1 nm to 50 nm, and
the second layer has a thickness of 5 nm to 300 nm.

7. The anti-reflective film according to claim 1,
wherein the solid inorganic nanoparticles has a diameter of 5 to 100 nm, and
the hollow inorganic nanoparticles has a diameter of 1 to 200 nm.

8. The anti-reflective film according to claim 1,
wherein a density of the solid inorganic nanoparticles is at least 0.50 g/cm³ higher than that of the hollow inorganic nanoparticles.

9. The anti-reflective film according to claim 1,
wherein each of the solid inorganic nanoparticles and the hollow inorganic nanoparticles contains one or more reactive functional groups selected from the group consisting of a (meth)acrylate group, an epoxide group, a vinyl group, and a thiol group on a surface thereof.

10. The anti-reflective film according to claim 1,
wherein the binder resin contained in the low-refractive layer contains a cross-linked (co)polymer formed from cross-linking a (co)polymer of a photopolymerizable compound and a fluorine-containing compound including a photoreactive functional group.

11. The anti-reflective film of claim 10, wherein the fluorine-containing compound including the photoreactive functional group has a weight average molecular weight of 2000 to 200,000.

12. The anti-reflective film according to claim 10,
wherein the binder resin contains 20 to 300 parts by weight of the fluorine-containing compound including the photoreactive functional group based on 100 parts by weight of the (co)polymer of the photopolymerizable compound.

13. The anti-reflective film according to claim 1, wherein the first layer included in the low refraction layer has a refractive index in a range of 1.420 to 1.600 when measured at a wavelength of 550 nm.

14. The anti-reflective film according to claim 13,
wherein the second layer included in the low refractive layer has a refractive index in a range of 1.200 to 1.410 when measured at a wavelength of 550 nm.

15. The anti-reflective film according to claim 1,
wherein the hard coating layer contains a binder resin containing a photocurable resin, and organic or inorganic fine particles dispersed in the binder resin.

16. The anti-reflective film of claim 15, having organic fine particles having a diameter of 1 to 10 μm or inorganic fine particles having a diameter of 1 nm to 500 nm dispersed in the binder resin.

17. The anti-reflective film according to claim 1,
wherein the hard coating layer contains a binder resin made of a photocurable resin, and an antistatic agent dispersed in the binder resin.

18. The anti-reflective film of claim 1, having a reflectance of 1.5% of less at a wavelength of 380 nm to 780 nm.

19. The anti-reflective film of claim 1, having a reflectance of 0.70% or less at a wavelength of 380 nm to 780 nm.

20. An anti-reflective film including: a hard coating layer and a low-refractive layer,
wherein the low-refractive layer contains hollow organic nanoparticles and solid inorganic nanoparticles that are dispersed in a binder resin, wherein the hollow inorganic particles are in a higher amount by weight than the solid inorganic particles
wherein the low-refractive layer includes a first layer containing at least 70 vol % of the total volume of solid inorganic nanoparticles dispersed in the binder resin and a second layer containing at least 70 vol % of the total volume of hollow inorganic nanoparticles dispersed in the binder resin, and
wherein the first layer has polarization ellipticity measured by ellipsometry using a Cauchy model represented by the following General Equation 1, in which A is 1.0 to 1.65:

$$n(\lambda) = A + \frac{B}{\lambda^2} + \frac{C}{\lambda^4} \qquad \text{[General Equation 1]}$$

wherein, in General Equation 1, $n(\lambda)$ is a refractive index at a wavelength of $\lambda$, $\lambda$ is in a range of 300 nm to 1800 nm, and A, B, and C are Cauchy parameters.

21. An anti-reflective film including: a hard coating layer and a low-refractive layer,
wherein the low-refractive layer contains hollow organic nanoparticles and solid inorganic nanoparticles that are dispersed in a binder resin, wherein the hollow inorganic particles are in a higher amount by weight than the solid inorganic particles
wherein the low-refractive layer includes a first layer containing at least 70 vol % of the total volume of solid inorganic nanoparticles dispersed in the binder resin and a second layer containing at least 70 vol % of the total volume of hollow inorganic nanoparticles dispersed in the binder resin, and has polarization ellipticity measured by ellipsometry for the first layer and the second layer included in the low-refractive layer using a Cauchy model represented by the following General Equation 1, in which the difference between the A value for the first layer and the A value for the second layer is 0.100 to 0.200:

$$n(\lambda) = A + \frac{B}{\lambda^2} + \frac{C}{\lambda^4} \quad \text{[General Equation 1]}$$

wherein, in General Equation 1, $n(\lambda)$ is a refractive index at a wavelength of $\lambda$, $\lambda$ is in a range of 300 nm to 1800 nm, and A, B, and C are Cauchy parameters.

\* \* \* \* \*

UNITED STATES PATENT AND TRADEMARK OFFICE
CERTIFICATE OF CORRECTION

| | | |
|---|---|---|
| PATENT NO. | : 10,222,510 B2 | Page 1 of 1 |
| APPLICATION NO. | : 15/554966 | |
| DATED | : March 5, 2019 | |
| INVENTOR(S) | : In Young Song | |

It is certified that error appears in the above-identified patent and that said Letters Patent is hereby corrected as shown below:

On the Title Page

In Item (73), under Assignee: "LG CHEM, LTD, SEOUL, REPUBLIC OF KOREA" should read as -- LG CHEM, LTD., SEOUL, REPUBLIC OF KOREA --.

Signed and Sealed this
Twelfth Day of May, 2020

Andrei Iancu
*Director of the United States Patent and Trademark Office*